(12) United States Patent
Ahmad et al.

(10) Patent No.: US 7,238,702 B2
(45) Date of Patent: Jul. 3, 2007

(54) DIHYDROQUINAZOLINONES AS 5HT MODULATORS

(75) Inventors: Saleem Ahmad, Wall, NJ (US); Khehyong Ngu, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/350,997

(22) Filed: Feb. 9, 2006

(65) Prior Publication Data

US 2006/0178386 A1    Aug. 10, 2006

Related U.S. Application Data

(60) Provisional application No. 60/651,833, filed on Feb. 10, 2005.

(51) Int. Cl.
| | |
|---|---|
| *A01N 43/54* | (2006.01) |
| *A61K 31/505* | (2006.01) |
| *A61K 31/55* | (2006.01) |
| *A61K 31/495* | (2006.01) |
| *C07D 239/00* | (2006.01) |
| *C07D 487/00* | (2006.01) |

(52) U.S. Cl. ............... 514/267; 544/250; 540/497; 514/220; 514/250

(58) Field of Classification Search ............... None
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,572,912 A | 2/1986 | Yoshioka et al. |
| 4,639,436 A | 1/1987 | Junge et al. |
| 4,681,893 A | 7/1987 | Roth |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,447,954 A | 9/1995 | Gribble et al. |
| 5,488,064 A | 1/1996 | Sher |
| 5,491,134 A | 2/1996 | Sher et al. |
| 5,541,204 A | 7/1996 | Sher et al. |
| 5,594,016 A | 1/1997 | Ueno et al. |
| 5,612,359 A | 3/1997 | Murugesan |
| 5,686,104 A | 11/1997 | Mills et al. |
| 5,698,527 A | 12/1997 | Kim |
| 5,712,396 A | 1/1998 | Magnin et al. |
| 5,753,675 A | 5/1998 | Wattanasin |
| 5,770,615 A | 6/1998 | Cheng et al. |
| 5,776,983 A | 7/1998 | Washburn et al. |
| 5,990,109 A | 11/1999 | Chen et al. |
| 6,043,265 A | 3/2000 | Murugesan et al. |
| 6,184,231 B1 | 2/2001 | Hewawasam et al. |
| 6,358,950 B1 | 3/2002 | He et al. |
| 6,362,180 B1 | 3/2002 | Wilde et al. |
| 6,395,767 B2 | 5/2002 | Robl et al. |
| 6,399,609 B1 | 6/2002 | Wilde |
| 6,414,002 B1 | 7/2002 | Cheng et al. |
| 6,414,126 B1 | 7/2002 | Ellsworth et al. |
| 6,448,261 B1 | 9/2002 | Bakthavatchalam et al. |
| 6,515,005 B2 | 2/2003 | Dubowchik et al. |
| 6,515,117 B2 | 2/2003 | Ellsworth et al. |
| 6,518,271 B1 | 2/2003 | Gilligan et al. |
| 6,521,636 B1 | 2/2003 | Gilligan et al. |
| 6,525,056 B2 | 2/2003 | Arvanitis et al. |
| 6,573,287 B2 | 6/2003 | Sulsky et al. |
| 6,579,876 B2 | 6/2003 | Gilligan et al. |
| 6,589,952 B2 | 7/2003 | Bakthavatchalam et al. |
| 6,630,476 B2 | 10/2003 | Bakthavatchalam et al. |
| 6,635,626 B1 | 10/2003 | Barrish et al. |
| 6,642,230 B2 | 11/2003 | Wilde et al. |

FOREIGN PATENT DOCUMENTS

| | | |
|---|---|---|
| DE | 196 22 222 | 12/1997 |
| EP | 0 675 714 | 10/1995 |

(Continued)

OTHER PUBLICATIONS

Samoylenko, V.P., Synthesis of Novel Tricyclic Derivatives of 7-azabenorobornene System, Tetrahedron, 58, 6103-6110 (2002).*

(Continued)

*Primary Examiner*—James O. Wilson
*Assistant Examiner*—Erich A. Leeser
(74) *Attorney, Agent, or Firm*—Sammy G. Duncan, Jr.

(57) ABSTRACT

The present invention relates to modulators of serotonin receptors, pharmaceutical compositions containing such modulators and methods for treating obesity using such compounds and compositions.

8 Claims, No Drawings

FOREIGN PATENT DOCUMENTS

| EP | 0 818 448 | 1/1998 |
|---|---|---|
| EP | 0 992 496 | 4/2000 |
| EP | 1 022 272 | 7/2000 |
| GB | 2 304 106 | 3/1997 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO99/42456 | 8/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/50574 | 8/2000 |
| WO | WO 02/076973 | 10/2002 |
| WO | WO 02/083636 | 10/2002 |
| WO | WO 03/072197 | 9/2003 |
| WO | WO 2004/094425 | 11/2004 |

OTHER PUBLICATIONS

Berridge, M. et al., "Lithium amplifies agonist-dependent phosphatidylinositol responses in brain and salivary glands", Biochem. J., vol. 206, pp. 587-595 (1982).

Biller, S. et al., "Squalene Synthase Inhibitors", Current Pharmaceutical Design, vol. 2, pp. 1-40 (1996).

Biller, S. et al., "Isoprenoid (Phosphinylmethyl) phosphonates as Inhibitors of Squalene Synthetase", Journal of Medicinal Chemistry, vol. 31(10), pp. 1869-1871 (1988).

Chojnacka-Wojcik, E. et al., "Involvement of 5-$HT_{2C}$ Receptors in the m-CPP-Induced antinociception in Mice", Pol. J. Pharmacol., vol. 46, pp. 423-428 (1994).

Corey, E. et al., "Application of Unreactive Analogs of Terpenoid Pyrophosphates to Studies of Multistep Biosynthesis. Demonstration that "Presqualene Pyrophosphate" is an essential Intermediate on the Path to Squalene", J. of the American Chemical Soc., vol. 98(5), pp. 1292-1293 (1976).

Cryan, J. et al., "Antidepressant-Like Behavioral Effects Mediated by 5-Hydroxytryptamine$_{2c}$ Receptors[1]", The J. of Pharmacology & Experimental Therapeutics, vol. 295(3), pp. 1120-1126 (2000).

DiMatteo, V. et al., "Role of 5-$HT_{2c}$ receptors in the control of central dopamine function", TRENDS in Pharmacological Sciences, vol. 22(5), pp. 229-232 (2001).

Egan, C. et al., "Agonist activity of LSD and lisuride at cloned $5HT_{2A}$ and $5HT_{2C}$ receptors", Psychopharmacology, vol. 136, pp. 409-414 (1998).

Fitzgerald, L. et al., "High-Affinity Agonist binding Correlates with Efficacy (Intrinsic Activity) at the Human Serotonin 5-$HT_{2A}$ and 5-$HT_{2c}$ Receptors: Evidence Favoring the Ternary Complex and Two-State Models of Agonist Action", J. of Neurochemistry, vol. 72(5), pp. 2127-2134 (1999).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30, (1998).

Glennon, R. et al., "[$^{125}$I]-1-(2,5-Dimethoxy-4-iodophenyl)-2-amino-propane: An Iodinated Radioligand that specifically Labels the Agonist High-Affinity State of 5-$HT_2$ Serotonin Receptors", J. Med. Chem., vol. 31, pp. 5-7 (1988).

Grottick, A. et al., "Studies to Investigate the Role of 5-$HT_{2C}$ Receptors on Cocaine- and Food-Maintained Behavior[1]", The J. of Pharmacology and Experimental Therapeutics, vol. 295(3), pp. 1183-1191 (2000).

Grottick, A. et al., "Activation of 5-$HT_{2C}$ receptors reduces the locomotor and rewarding effects of nicotine", Psychopharmacology, vol. 157, pp. 292-298 (2001).

Hara, S., "Ileal $Na^+$/bile acid cotransporter inhibitors", Drugs of the Future, vol. 24(4), pp. 425-430 (1999).

Hoffman, B. et al., "Distribution of serotonin 5-$HT_{1C}$ receptor mRNA in adult rat brain", FEBS Letters, vol. 247(2), pp. 453-462 (1989).

Hollenbaugh, D. et al., "Cleavable CD40Ig fusion proteins and the binding to sgp39", J. of Immunological Methods, vol. 188, pp. 1-7 (1995).

Hollenbaugh, D. et al., "The human T cell antigen gp39, a member of the TNF gene family, is a ligand for the CD40 receptor: expression of a soluble form of gp39 with B cell co-stimulatory activity", The EMBO Journal, vol. 11(12), pp. 4313-4321 (1992).

Horlick, R. et al., "Rapid generation of Stable Cell Lines Expressing Corticotropin-Releasing Hormone Receptor for Drug Discovery", Protein Expression and Purification, vol. 9, pp. 301-308, (1997).

Hoyer, D. et al., "VII. International Union of Pharmacology Classification of Receptors for 5-Hydroxytryptamine (Serotonin)", Pharmacological Reviews, vol. 46(2), pp. 157-203 (1994).

Krause, B. et al., "ACAT Inhibitors: Physiologic Mechanisms for Hypolipidemic and Anti-Atherosclerotic Activities in Experimental Animals", Inflammation: Mediators and Pathways, pp. 173-198 (1995).

Leonhardt, S. et al., "Molecular Pharmacological Differences in the Interaction of Serotonin with 5-Hydroxytryptamine$_{1c}$ and 5-Hydroxytryptamine$_2$ Receptors", Molecular Pharmacology, vol. 42, pp. 328-335 (1992).

Lucaites, V. et al., "Receptor Subtype and Density Determine the Coupling Repertoire of the 5-$HT_2$ Receptor Subfamily", Life Sciences, vol. 59(13), pp. 1081-1095 (1996).

Mazzola-Pomietto, P. et al., "Evidence that m-chlorophenylpiperazine-induced hyperthermia in rats is mediated by stimulation of 5-$HT_{2c}$ receptors", Psychopharmacology, vol. 123, pp. 333-339 (1996).

McClard, R. et al., "Novel Phosphonylphosphinyl (P-C-P-C-) Analogues of Biochemically Interesting Dephosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Millan, M. et al., "5-$HT_{2c}$ receptors mediate penile erections in rats: actions of novel and selective agonists and antagonists", European Journal of Pharmacology, vol. 325, pp. 9-12 (1997).

Moreland, L. et al., "Treatment of Rheumatoid Arthritis with a Recombinant Human Tumor Necrosis factor Receptor (p75)-Fc Fusion Protein", The New England Journal of Medicine, vol. 337(3), pp. 141-147 (1997).

Nicolosi, R. et al., "The ACAT inhibitor, CI-1011 is effective in the prevention and regression of aortic fatty streak area in hamsters", Atherosclerosis, vol. 137, pp. 77-85 (1998).

Nonogaki, K. et al., "Leptin-independent hyperphagia and type 2 diabetes in mice with a mutated serotonin 5-$HT_{2c}$ receptor gene", Nature Medicine, vol. 4(10), pp. 1152-1156 (1998).

Ortiz de Montellano, P. et al., "Inhibition of Squalene Synthetase by Farnesyl Pyrophosphate Analogues[1]", J. of Medicinal Chemistry, vol. 20(2), pp. 243-248 (1977).

Rittenhouse, P. et al., "Evidence that ACTH Secretion is regulated by Serotonin $_{2A/AC}$ (5-$HT_{2A/2C}$) Receptors", J. of Pharmacology and Experimental Therapeutics, vol. 271(3), pp. 1647-1655 (1994).

Rosenblum, S. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Salisbury, B. et al., "Hypocholesterolemic activity of a novel inhibitor of cholesterol absorption, SCH 48461", Atherosclerosis, vol. 115, pp. 45-63 (1995).

Sharpley, A. et al., "Slow Wave Sleep in Humans: Role of 5-$HT_{2A}$ and 5-$HT_{2C}$ Receptors", Neuropharmacology, vol. 33(3/4) pp. 467-471 (1994).

Sliskovic, D. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor[1]", Bioorganic & Medicinal Chemistry Letters, vol. 6(1), pp. 47-50 (1996).

Sorbera, L. et al., "Avasimibe: Treatment of Lipoprotein Disorders ACAT Inhibitor", Drugs of the Future, vol. 24(1), pp. 9-15 (1999).

Stout, D., "Inhibitors of Acyl-CoA: Cholesterol O-Acyl Transferase (ACAT) as Hypocholesterolemic Agents. 6. The First Water-Soluble ACAT Inhibitor with Lipid-Regulating Activity. Inhibitors of Acyl-CoA: Cholesterol Acyltransferase (ACAT).7. Development of a Series of Substituted N-Phenyl-N-[(1-phenylcyclopentyl)-methyl] ureas with Enhanced Hypocholestrolemic Activity", Chemtracts-Organic Chemistry, vol. 8, pp. 359-362 (1995).

Vickers, S. et al., "Reduced satiating effect of d-fenfluramine in serotonin 5-$HT_{2c}$ receptor mutant mice", Psychopharmacology, vol. 143, pp. 309-314 (1999).

Vickers, S. et al., "Evidence that hypophagia induced by d-fenfluramine and d-norfenfluramine in the rat is mediated by 5-$HT_{2c}$ receptors", Neuropharmacology, vol. 41, pp. 200-209 (2001).

Vickers, S. et al., "Comparative effects of continuous infusion of mCPP, Ro 60-0175 and d-fenfluramine on food intake, water intake, body weight and locomotor activity in rats", British J. of Pharmacology, vol. 130, pp. 1305-1314 (2000).

Arnt; J., "Pharmacological Specificity of Conditioned Avoidance Response Inhibition in Rats: Inhibition by Neuroleptics and Correlation to Dopamine Receptor Blockade", ACTA Pharmacol, et Toxicol., vol. 51, pp. 321-329 (1982).

Costall, B. et al., "Detection of the Neuroleptic Properties of Clozapine, Sulpiride and Thioridazine", Psychopharmacologia, vol. 43, pp. 69-74 (1975).

Zigeuner, G. et al., "2-(1,2,3,4-Tetrahydro-4,4,6-trimethyl-2-thioxo-1-pyrimidine) benzoic acid and 2,3,4,4a-tetrahydro-3,3,4a-trimethyl-1-thioxo-1H, 6H-pyrimido[1,6-a] [3,1] benzoxazin-6-one" Monatshefte Fur Chemie, vol. 109(1), pp. 113-121 (1978).

* cited by examiner

DIHYDROQUINAZOLINONES AS 5HT MODULATORS

RELATED APPLICATION

This application claims priority benefit under Title 35 § 119(e) of U.S. Provisional Application No. 60/651,833, filed Feb. 10, 2005, the contents of which are herein incorporated by reference.

BACKGROUND OF THE INVENTION

The neurotransmitter/hormone serotonin (5-hydroxytryptamine, 5-HT) regulates many physiological processes via a group of at least 14 distinct receptors that are organized into 7 subfamilies (Hoyer, D., et al., Pharmacol. Rev., 46, 1994). The 5-$HT_2$ subfamily is composed of the 5-$HT_{2A}$, 5-$HT_{2B}$, and 5-$HT_{2C}$ receptors as determined by gene homology and pharmacological properties. There exists a substantial correlation for the relationship between 5-$HT_2$ receptor modulation and a variety of diseases and therapies. Prior to the early 1990's the 5-$HT_{2C}$ and 5-$HT_{2A}$ receptors were referred to as 5-$HT_{1C}$ and 5-$HT_2$, respectively.

The direct or indirect agonism or antagonism of 5-$HT_2$ receptors, either selectively or non-selectively, has been associated with the treatment of various central nervous system (CNS) disorders including obesity, depression, schizophrenia and bi-polar disorders. In the recent past the contribution of serotonergic activity to the mode of action of anti-obesity drugs has been well documented. Compounds that increase the overall basal tone of serotonin in the CNS have been developed as anorectic drugs. The serotonin releasing agents, such as fenfluramine, function by increasing the amount of serotonin present in the nerve synapse. These breakthrough treatments, however, are not without side effects. Due to the mechanism of action of serotonin releasing agents, they effect the activity of a number of serotonin receptor subtypes in a wide variety of organs including those not associated with the desired mechanism of action. This non-specific modulation of the serotonin family of receptors most likely plays a significant role in the side effect profile. In addition, these compounds or their metabolites often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

The 5-$HT_{2C}$ receptor is a G-protein coupled receptor. It is almost exclusively expressed in the central nervous system including the hypothalamus, hippocampus, amygdala, nucleus of the solitary tract, spinal cord, cortex, olfactory bulb, ventral tegmental area (VTA), nucleus accumbens and choroid plexus (Hoffman, B. and Mezey, E., FEBS Lett., 247, 1989). There is ample evidence to support the role of selective 5-$HT_{2C}$ receptor ligands in a number of disease therapies. 5-$HT_{2C}$ knockout mice develop a late stage obesity syndrome that is not reversed by fenfluramine or other direct acting 5-$HT_{2C}$ agonists such as mCPP (Nonogaki, K., et al., Nature Med., 4, 1998; Vickers, S., et. al., Psychopharmacology, 143, 1999). Administration of selective 5-$HT_{2C}$ agonists to rats causes a reduction in food intake and corresponding reduction in body weight (Vickers, S., et al., Br. J. Pharmacol., 130, 2000) and these responses can be blocked by administration of selective 5-$HT_{2C}$ antagonists (Vicker, S., et al., Neuropharmacol., 41, 2001). 5-$HT_{2C}$ receptor modulation in the hypothalamus can also influence thermoregulation (Mazzola-Pomietto, P, et al., Psychopharmacology, 123, 1996), sleep (Sharpley, A., et al., Neuropharmacology, 33, 1994), sexual behavior and neuroendocrine function (Rittenhouse, P. et al., J. Pharmacol. Exp. Ther., 271, 1994). Activation of 5-$HT_{2C}$ receptors in the VTA modulates the activity of dopaminergic neurons that are involved in aspects of depression (Di Matteo, V. et al., Trends Pharmacol. Sci., 22, 2001) and 5-$HT_{2C}$ receptor agonists such as WAY 161503, RO 60-0175 and RO 60-0332 are active in rodent models of depression (Cryan, J. and Lucki, I., J. Pharmacol. Exp. Ther., 295, 2000). 5-$HT_{2C}$ agonists have been reported to reduce the rewarding effects of nicotine administration in rats (Grottick, A., et al., Psychopharmacology, 157, 2001) and influences rodent responses to cocaine administration (Grottick, A., et al., J. Pharmacol. Exp. Ther., 295, 2000). Modulation of 5-$HT_{2C}$ receptors in the spinal cord can influence pain perception (Chojnacka-Wojcik, E., et al., Pol. J. Pharmacol., 46, 1994). There is also data indicating that the 5-$HT_{2C}$ receptor agonists mCPP and RO 60-0175 mediate penile erections in rats (Millan, M., et al., Eur J. Pharmacol. 325, 1997).

There remains a need to discover new compounds useful as serotonin receptor modulators, i.e. selective agonists and antagonists, which are useful in the control or prevention of central nervous system or peripheral disorders. As such, the present application discloses novel compounds which are useful as serotonin agonists and antagonists, and provide good in vitro potency.

DETAILED DESCRIPTION OF THE INVENTION

The present application provides novel compounds according to Formula I:

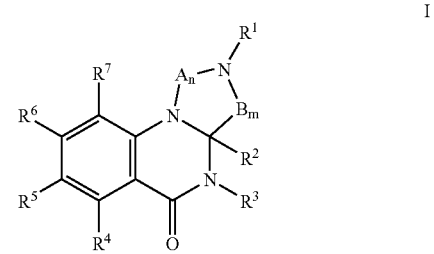

including stereoisomers and pharmaceutically acceptable salt forms thereof, wherein A, B, m, n, $R^1$, $R^2$, $R^3$, $R^4$, $R^5$, $R^6$ and $R^7$ are described herein. Additionally, the present application provides pharmaceutical compositions comprising at least one compound according to Formula I and optionally at least one other theapeutic agent. Finally, the present application provides methods of treating a disease or disorder that can be regulated by a serotonin modulator.

DEFINITIONS

The following definitions apply to the terms as used throughout this specification, unless otherwise limited in specific instances.

Unless otherwise indicated, the term "alkyl" as employed herein alone or as part of another group includes both straight and branched chain hydrocarbons, containing 1 to 40 carbons, preferably 1 to 20 carbons, more preferably 1 to 6 carbons, in the normal chain, such as, for example, methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "alkylene" as employed herein alone or as part of another group refers to alkyl linking groups above having single bonds for attachment to other groups at two different carbon atoms.

Unless otherwise indicated, the term "alkenyl" as used herein by itself or as part of another group refers to straight or branched chain radicals of 2 to 20 carbons, preferably 2 to 12 carbons, and more preferably 2 to 6 carbons in the normal chain, which include one or more double bonds in the normal chain, such as, for example, vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkenylene" and as employed herein alone or as part of another group refers to alkenyl linking groups, having single bonds for attachment at two different carbon atoms.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as, for example, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with one or more functional groups as defined above for alkyl.

The term "alkynylene" as employed herein alone or as part of another group refers to alkynyl linking groups, having single bonds for attachment at two different carbon atoms.

The term "halogen" or "halo" as used herein alone or as part of another group refers to chlorine, bromine, fluorine and iodine.

Unless otherwise indicated, the term "cycloalkyl" as employed herein alone or as part of another group refers to saturated or partially unsaturated (containing 1 or 2 double bonds) cyclic hydrocarbon groups containing 1 to 3 rings, including monocyclic alkyl, bicyclic alkyl and tricyclic alkyl, containing a total of 3 to 20 carbons forming the rings, preferably 4 to 10 carbons, forming the ring such as, for example, cyclopropyl, cyclobutyl, cyclopentyl, cyclohexyl, cycloheptyl, cyclooctyl, cyclodecyl, cyclododecyl, cyclohexenyl,

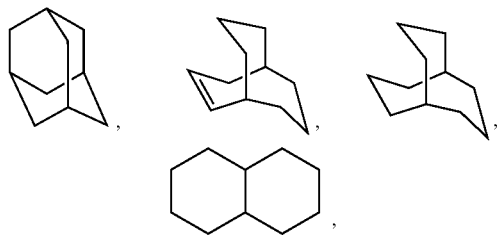

wherein the cycloalkyl may be fused to 1 aromatic ring as described for aryl.

The term "heterocyclyl", as used herein, refers to an unsubstituted or substituted stable 4-, 5-, 6- or 7-membered monocyclic ring system which may be saturated or unsaturated, and which consists of carbon atoms and from one to four heteroatoms selected from N, O, S, SO and/or $SO_2$ group, wherein the nitrogen heteroatoms may optionally be oxidized, and the nitrogen heteroatom may optionally be quaternized. The heterocyclic ring may be attached at any heteroatom or carbon atom which results in the creation of a stable structure such as, for example, piperidinyl, piperazinyl, oxopiperazinyl, oxopiperidinyl and oxadiazolyl.

The term "aryl" as employed herein alone or as part of another group refers to monocyclic and bicyclic aromatic groups containing 6 to 10 carbons in the ring portion such as, for example, phenyl or naphthyl and may optionally include one to three additional rings fused to "aryl" such as, for example, aryl, cycloalkyl, heteroaryl or cycloheteroalkyl rings.

The term "heteroaryl" as used herein refers to a 5-, 6- or 7-membered aromatic heterocyclic ring which contains one or more heteroatoms selected from nitrogen, sulfur, oxygen and/or a SO or $SO_2$ group. Such rings may be fused to another ring such as, for example, cycloalkyl, cycloheteroalkyl, aryl or heteroaryl and include possible N-oxides.

The term "oxy" as used herein as part of another group refers to an oxygen atom serving as a linker between two groups such as, for example, hydroxy, oxyalkyl, alkenyl, alyalkynyl, oxyperfluoroalkyl, oxyaryl, oxyheteroaryl, oxycarboalkyl, oxycarboalkenyl, oxycarboalkynyl, oxycarboaryl, oxycarboheteroaryl, oxycarbocycloalkyl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl and aminocarboxyheteroaryl.

The term "carbo" as used herein as part of another group refers to a carbonyl (C═O) group serving as a linker between two groups such as, for example, carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl and aminocarboaminoheteroaryl.

The term "thio" as used herein as part of another group refers to a sulfur atom serving as a linker between two groups such as, for example, thioalkyl, thioalkenyl, thioalkynyl, thioaryl, thioheteroaryl and thiocycloalkyl.

The term "perfluoro" as used herein as part of another group refers to a group wherein more than one hyrdogen atom attached to one or more carbon atoms in the group has been replaced with a fluorine atom such as, for example, perfluoroalkyl, perfluoroalkenyl, perfluoroalkynyl and oxyperfluoroalkyl.

The term "amino" as used herein alone or as part of another group refers to a nitrogen atom that may be either terminal or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine such as, for example, amino, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, sulfoalkyl, sulfoalkenyl, sulfoalkynyl, sulfoaryl, sulfocycloalkyl, sulfoheterocyclyl and sulfoheteroaryl.

The term "nitrile" as used herein refers to a cyano (a carbon atom triple-bonded to a nitrogen atom) group.

The term "sulfinyl" as used herein as part of another group refers to an —SO— group such as, for example, sulfinylalkyl, sulfinylalkenyl, sulfinylalkynyl, sulfinylaryl, sulfinylcycloalkyl, sulfinylheterocyclyl and sulfinylheteroaryl.

The term "sulfonyl" as used herein as part of another group refers to an —SO$_2$— group such as, for example, sulfonylalkyl, sulfonylalkenyl, sulfonylalkynyl, sulfonylaryl, sulfonylcycloalkyl, sulfonylheterocyclyl and sulfonylheteroaryl.

An administration of a therapeutic agent of the application includes administration of a therapeutically effective amount of the agent of the application. The term "therapeutically effective amount" as used herein refers to an amount of a therapeutic agent to treat or prevent a condition treatable by administration of a composition of the application. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

Any compound that can be converted in vivo to provide the bioactive agent (i.e., the compound of formula I) is a prodrug within the scope and spirit of the application.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:
a) *The Practice of Medicinal Chemistry*, Camille G. Wermuth et al., Ch. 31 (Academic Press, 1996);
b) *Design of Prodrugs*, edited by H. Bundgaard, (Elsevier, 1985); and
c) *A Textbook of Drug Design and Development*, P. Krogsgaard-Larson and H. Bundgaard, eds. Ch. 5, pp. 113-191 (Harwood Academic Publishers, 1991). Said references are incorporated herein by reference.

All stereoisomers of the compounds of the instant application are contemplated, either in admixture or in pure or substantially pure form. The compounds of the present application can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques or fractional crystallization.

The pharmaceutically acceptable salts of the compounds of formula I of the application include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, stearate and salts of naturally occurring amino acids such as arginine, lysine, alanine and the like, and prodrug esters thereof.

SYNTHESIS

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

Compounds of Formula I can be prepared as depicted in Schemes 1 to 3; wherein $R^1$, $R^2$, $R^3$, $R^4$, $R^5$, $R^6$, $R^7$, A, B and m are as defined for compounds of Formula I, x is 1 or 2, and $R^8$, $R^9$ and $R^{10}$ are as descibed in the definitions for $R^1$, $R^{1a}$, $R^{1b}$, $R^{1c}$, $R^{1d}$ and $R^2$.

Thus, cyclocondensation of various ortho aminobenzamides 1 and N-protected aminoaldehydes 2 in the presence of catalytic amounts of an acid such as p-toluenesulfonic acid in solvents such as toluene or benzene at reflux temperatures affords 3 (Scheme 1). Treatment of 3 with various unsaturated organic halides 4 (or tosylates etc.) in the presence of a base such as sodium or potassium carbonate in solvents such as DMF, DMA or NMP affords 5. Oxidative cleavage of the olefinic bond of 5 by using catalytic amounts of osmium tetroxide in the presence of sodium periodate in THF and water affords a mixture contaning aldehyde 6 and hemi-aminal 7, which upon treatment with a reducing agent such as triethylsilane in the presence of an acid such as TFA affords 8. Removal of the N-protecting group affords compounds of Formula Ia ($R^1$=H).

Certain compounds of Formula Ib ($R^1$=other than H) can be prepared by treating compounds of formula 8 (where protect.=Cbz) with an aldehyde or a ketone ($R^9R^{10}CO$) in the presence of hydrogen and a catalyst such as Palladium on carbon in solvents such as methanol or ethanol.

Certain compounds of Formula Ic ($R^3$=other than H) can be prepared from compound 8 by treatment with an electrophile such as $R^3I$ in the presence of a base (e.g. NaH) prior to removal of the protecting group (Scheme 1).

SCHEME 1

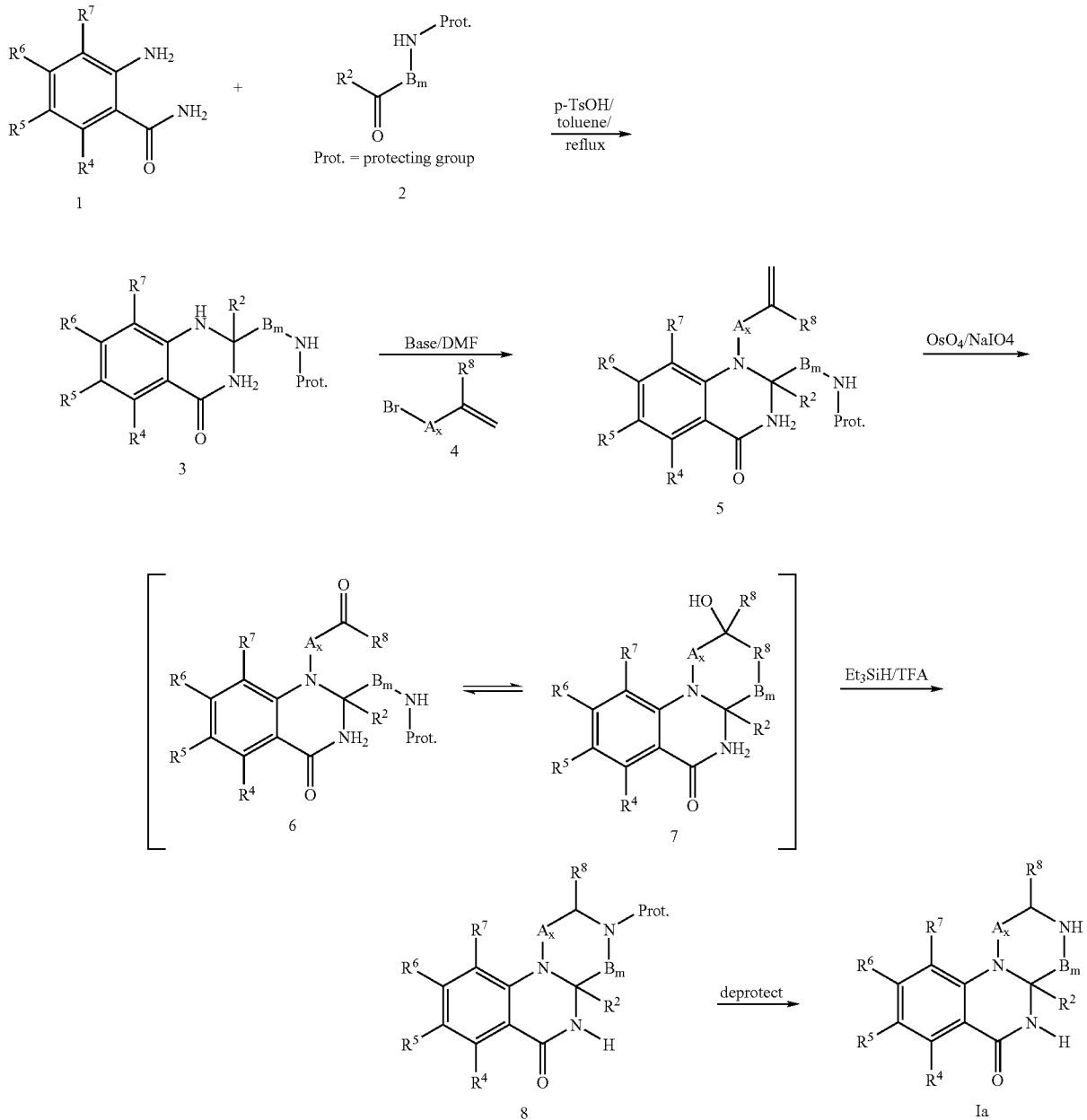

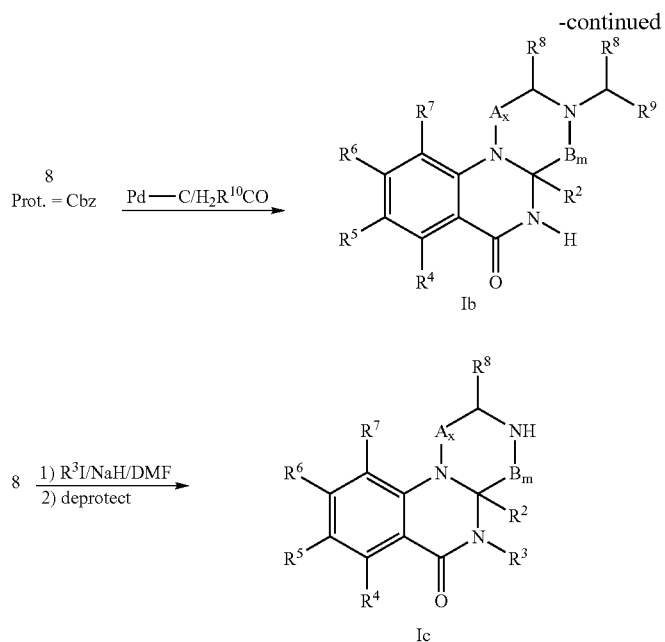

Compound 3 can also be prepared as outlined in Scheme 2 by reaction of ortho nitrobenzamides 9 with compound 2 in the presence of a reducing agent such a iron powder and an acid (e.g. acetic acid). Compound 5 can also be prepared by reacting ortho halobenzamodes 10 with amines 11 in the presence of a base (e.g. potassium carbonate, sodium carbonate, etc.) in solvents such as DMF, DMA or NMP. The resulting adduct 12 can be converted to the intermediate 5 via cyclocondensation with a protected amino aldehyde 2 as described previously for Scheme 1.

Certain compounds of Formula Id (where n=3) can be prepared as described in Scheme 3. Thus treatment of compound 5 with borane followed by sodium hydroxide and hydrogen peroxide affords 13 which can be oxididized to 14 by using reagents such as Dess-Martin's periodinane. Compound 14 can be converted to the compound of Formula Ic by treatment with triethyl silane and TFA.

SCHEME 2

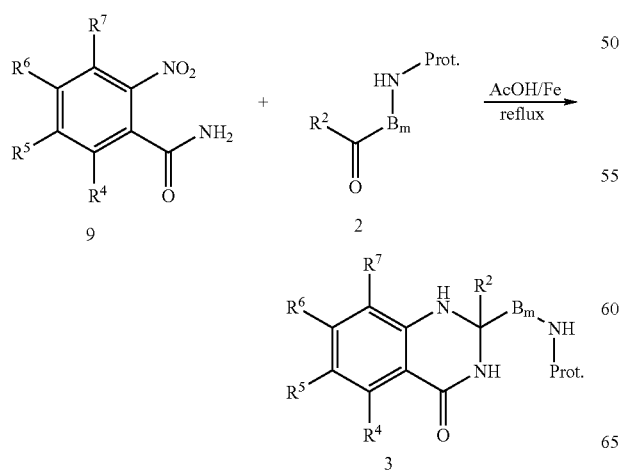

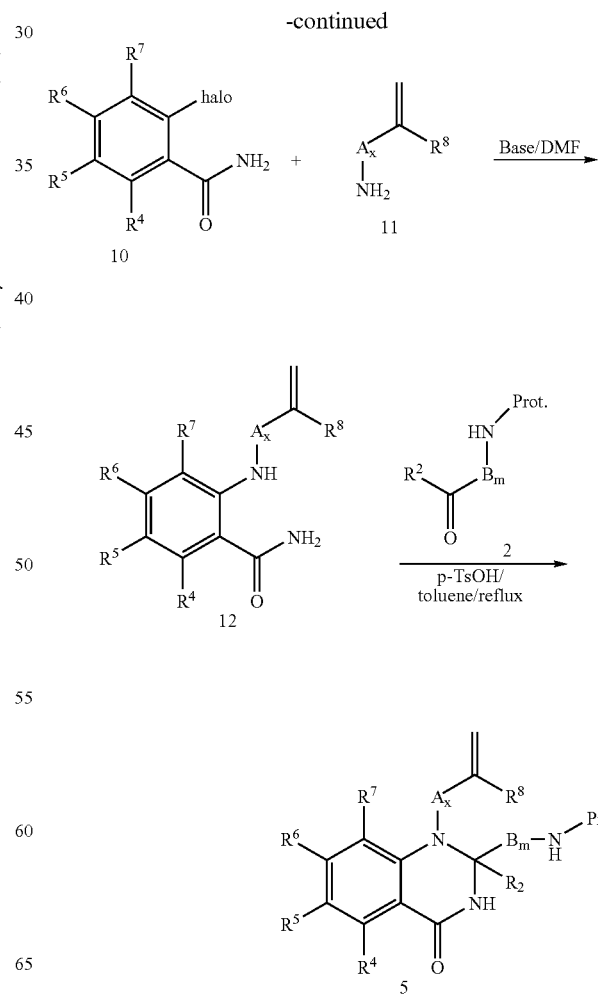

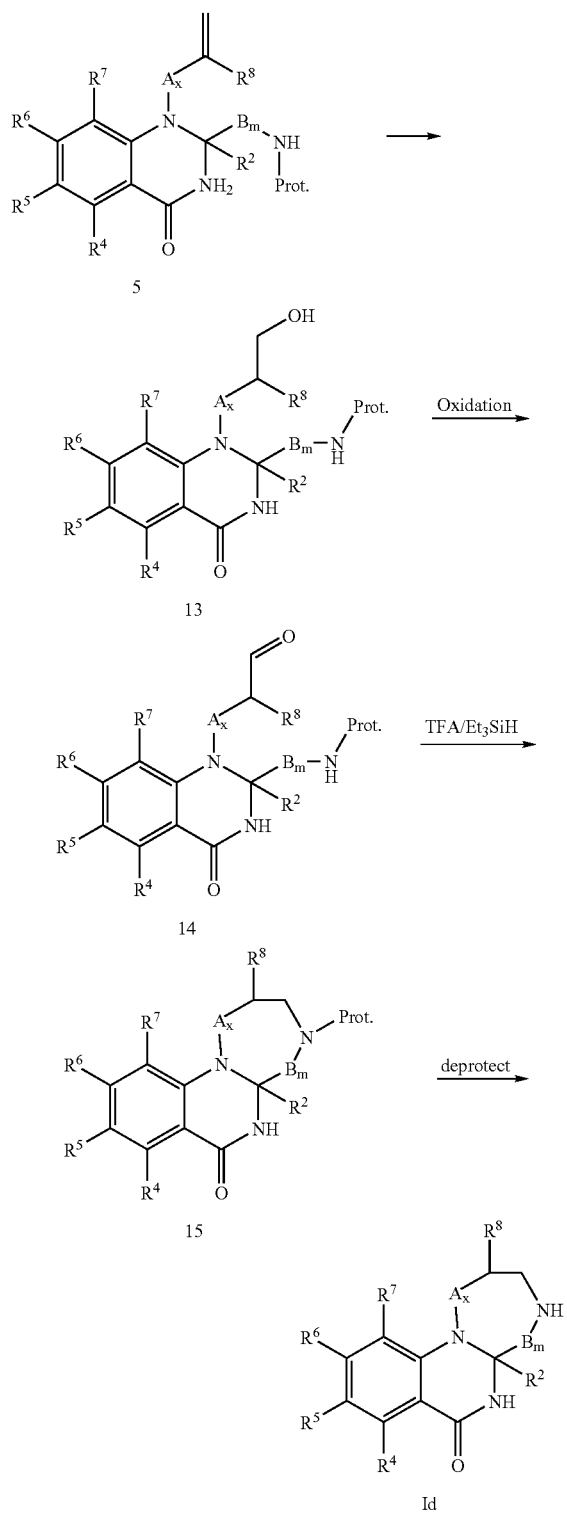

SCHEME 3

UTILITIES AND COMBINATIONS

Utilities

The compounds of the present application are 5HT modulators, and include compounds which are, for example, selective agonists, partial agonists, antagonists or partial antagonists of the $5HT_{2C}$ receptor. Accordingly, the compounds of the present application may be useful for the treatment or prevention of diseases and disorders associated with 5HT receptor activity. Preferably, compounds of the present application possess activity as agonists of the $5HT_{2C}$ receptor, and may be used in the treatment of diseases or disorders associated with the activity of the $5HT_{2C}$ receptor.

Accordingly, the compounds of the present application can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, impaired glucose hemostatsis, insulin resistance, hypercholesterolemia, hypertriglyceridemia, cholelithiasis and sleep disorders, dislipidemic conditions, bulimia nervosa and compulsive eating disorders); pain; sleep disorders and psychiatric disorders, such as substance abuse, depression, anxiety, psychosis, mania and schizophrenia.

These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of cardiac dysfunction (e.g., associated with valvular disease, myocardial infarction, cardiac hypertrophy or congestive heart failure); and improvement of the overall pulmonary function; transplant rejection; rheumatoid arthritis; osteoarthritis; fibromyalgia; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury. These compounds could also be used for treatment of sexual dysfunction and erectogenesis.

Compounds useful in the treatment of appetite or motivational disorders regulate desires to consume sugars, carbohydrates, alcohol or drugs and more generally to regulate the consumption of ingredients with hedonic value. In the present description and in the claims, appetite disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present application therefore further relates to the use of a $5HT_{2C}$ receptor agonist for the treatment of bulimia and obesity, including obesity associated with type II diabetes (non-insulin-dependent diabetes), or more generally any disease resulting in the patient becoming overweight. Overweight and obesity, as described herein, is defined by a body mass index ($kg/m^2$) for example, at least 26. It may be due to any cause, whether genetic or environmental, including overeating and bulimia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present application may also be useful in treating substance abuse disorders, including substance dependence or abuse without physiological dependence. Substances of abuse include alcohol, amphetamines (or amphetamine-like substances), caffeine, *cannabis*, cocaine, hallucinogens, inhalants, nicotine, opioids, phencyclidine (or phencyclidine-like compounds), sedative-hypnotics or benzodiazepines, and other (or unknown) substances and combinations of the above. The terms "substance abuse disorders" also includes drug, nicotine or alcohol withdrawal syndromes and substance-induced anxiety or mood disorder with onset during withdrawal.

Compounds in the present application may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, attention deficit-hyperactivity disorder, HIV, cardiovascular disease such as ischemia or stroke, and head trauma as well as age-related cognitive decline. Dementias are diseases that include memory loss and additional intellectual impairment separate from memory. $5HT_{2C}$ modulators may also be useful in treating cognitive impairments related to attentional deficits, such as attention deficit-hyperactivity disorders.

Compounds in the present application may also be useful in treating diseases associated with dysfunction of brain dopaminergic systems, such as Parkinson's Disease and substance abuse disorders. Parkinson's Disease is a neurodenerative movement disorder characterized by bradykinesia and tremor.

Combinations

The present application includes within its scope pharmaceutical compositions comprising, as an active ingredient, a therapeutically effective amount of at least one of the compounds of formula I, alone or in combination with a pharmaceutical carrier or diluent. Optionally, compounds of the present application can be used alone, in combination with other suitable therapeutic agents useful in the treatment of the aforementioned disorders including: anti-obesity agents; anti-diabetic agents, appetite suppressants; cholesterol/lipid-lowering agents, cognition enhancing agents, agents used to treat neurodegeneration, agents used to treat respiratory conditions, agents used to treat bowel disorders, anti-inflammatory agents; anti-anxiety agents; anti-depressants; anti-psychotic agents; sedatives; hypnotics; anti-hypertensive agents; anti-tumor agents and analgesics.

Such other therapeutic agent(s) may be administered prior to, simultaneously with, or following the administration of the $5HT_{2C}$ modulators in accordance with the application.

Examples of suitable anti-obesity agents for use in combination with the compounds of the present application include leptin and leptin-sensitizing agents, melanocortin receptor (MC4R) agonists, agouti-related peptide (AGRP) antagonists, melanin-concentrating hormone receptor (MCHR) antagonists, growth hormone secretagogue receptor (GHSR) antagonists, orexin antagonists, CCK agonists, GLP-1 agonists, NPY1 or NPY5 antagonsits, NPY2 or NPY4 modulators, corticotropin releasing factor agonists, histamine receptor-3 (H3) modulators, aP2 inhibitors, PPAR gamma modulators, PPAR delta modulators, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio), a lipase inhibitor, such as orlistat or ATL-962 (Alizyme), leptinergics, adiponectin modulating agents, cannabinoid-1 receptor antagonists, such as SR-141716 (Sanofi) or SLV-319 (Solvay), acetyl CoA carboxylase (ACC) inhibitors as disclosed in International patent application WO 03/072197 and monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), axokine (Regeneron).

Examples of suitable anti-diabetic agents for use in combination with the compounds of the present application include: insulin, which may include short- and long-lasting forms as well as oral and inhaled forms, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists such as muraglitizar described in Bristol-Myers Squibb U.S. Pat. No. 6,414,002, dipeptidyl peptidase IV (DP4) inhibitors such as saxagliptan described in Bristol-Myers Squibb U.S. Pat. Nos. 6,395,767 and 6,573,287, SGLT2 inhibitors such as the compounds described in Bristol-Myers Squibb U.S. Pat. Nos. 6,414,126 and 6,515,117, glycogen phosphorylase inhibitors, and/or meglitinides, as well as insulin, and/or glucagon-like peptide-1 (GLP-1), and/or a PTP-1B inhibitor (protein tyrosine phosphatase-1B inhibitor).

The antidiabetic agent may be glucokinase inhibitors, 11 β HSD inhibitors or oral antihyperglycemic agents, which is preferably a biguanide such as metformin or phenformin or salts thereof, preferably metformin HCl. Where the antidiabetic agent is a biguanide, the compounds of the present application will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present application may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's REZULIN, disclosed in U.S. Pat. No. 4,572,912), rosiglitazone (SKB), pioglitazone (Takeda), Mitsubishi's MCC-555

(disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present application may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NKs-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40(1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J. A. C. S., 1987, 109, 5544, cyclopropanes reported by Capson, T. L., PhD dissertation, June, 1987, Dept. Med. Chem. U of Utah, Abstract, Table of Contents, pp 16, 17, 40-43, 48-51, Summary, pyrrolidine derivatives as disclosed by Sasyou, et al, WO 02/083636 and N-aryl-substituted cyclic amine derivatives disclosed by Okada et al, WO 02/076973.

Other hypolipidemic agents suitable for use herein include, but are not limited to, fibric acid derivatives, α PPAR agonists, such as fenofibrate, gemfibrozil, clofibrate, bezafibrate, ciprofibrate, clinofibrate and the like, probucol, and related compounds as disclosed in U.S. Pat. No. 3,674,836, probucol, phenylfibrate and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future 24, 9-15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137 (1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's Torcetrapib® as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in Drugs of the Future, 24, 425-430 (1999). The ATP citrate lyase inhibitor which may be employed in the combination of the application may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof, and inhibitors or lipid synthesis enzymes such as, for example, ACC, FAS, DGAT, MGAT, GPAT, AMP kinase, CPT1 and SCD1. Preferred dislipidemic agents are pravastatin, lovastatin, simvastatin, atorvastatin, fluvastatin, pitavastatin, rosuvastatin, fenofibrate and Pfizer's Torcetrapib® as well as niacin and/or cholestagel.

The compounds of the present application may be employed in combination with anti-hypertensive agents. Examples of suitable anti-hypertensive agents for use in combination with the compounds of the present application include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan, candasartan and talmisartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

$5HT_{2C}$ modulators could be useful in treating other diseases associated with obesity, including sleep disorders. Therefore, the compounds described in the present application could be used in combination with therapeutics for treating sleep disorders. Examples of suitable therapies for treatment of sleeping disorders for use in combination with the compounds of the present application include melatonin analogs, melatonin receptor agonists, ML 1 B agonists. GABA A receptor agonists such as barbiturates (e.g., amobarbital, aprobarbital, butabarbital, mephobarbital, pentobarbital, phenobarbital, secobarbital and talbutal), benzodiazepines (e.g., diazepam, lorazepam, oxazepam, alprazolam, chlordiazepoxide, clonazepam, chlorazepate, halazepam and prazepam), also specifically including triazolam (Halcion). Other agents for treating sleep disorders include zolpidem (Ambien) and Neurocrine's indiplon.

$5HT_{2C}$ modulators may reduce or ameliorate substance abuse or addictive disorders. Therefore, combination of $5HT_{2C}$ modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion and opiate antagonists.

$5HT_{2C}$ modulators may reduce anxiety or depression; therefore, the compounds described in this application may be used in combination with anti-anxiety agents or antidepressants. Examples of suitable anti-anxiety agents for use in combination with the compounds of the present application include benzodiazepines (e.g., diazepam, lorazepam, oxazepam, alprazolam, chlordiazepoxide, clonazepam, chlorazepate, halazepam and prazepam), $5HT_{1A}$ receptor agonists (e.g., buspirone, flesinoxan, gepirone, ipsapirone and serzone), corticotropin releasing factor (CRF) antagonists and SSRI's.

Examples of suitable classes of anti-depressants for use in combination with the compounds of the present application include norepinephrine reuptake inhibitors (tertiary and secondary amine tricyclics), selective serotonin reuptake inhibitors (SSRIs) (fluoxetine, fluvoxamine, paroxetine, citalopram and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists (Britsol-Myers Squibb U.S. Pat. Nos. 6,642,230; 6,630,476; 6,589,952; 6,579,876; 6,525,056; 6,521,636; 6,518,271; 6,515,005; 6,448,261; 6,399,609; 6,362,180; and 6,358,950), alpha-adrenoreceptor antagonists, and atypical antidepressants (bupropion, lithium, nefazodone, trazodone and viloxazine).

The combination of a conventional antipsychotic drug with a $5HT_{2C}$ modulator could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present application include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present application include loxapine, sulpiride and risperidone.

Combination of the compounds in the present application with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present application include the antipsychotics mentioned above, as well as dopamine receptor antagonists, muscarinic receptor agonists, $5HT_{2A}$ receptor antagonists and $5HT_{2A}$/dopamine receptor antagonists or partial agonists (e.g., olanzepine, aripiprazole, risperidone, ziprasidone).

The compounds described in the present application could be used to enhance the effects of cognition-enhancing agents, such as acetylcholinesterase inhibitors (e.g., tacrine the active agent in Cognex®), ADHD agents (e.g. methylphenidate, atomoxetine the active agent in Strattera® and histamine 3 antagonists), muscarinic receptor-1 agonists (e.g., milameline), nicotinic agonists, glutamic acid receptor (AMPA and NMDA) modulators such as memantine, and nootropic agents (e.g., piracetam, levetiracetam). Examples of suitable therapies for treatment of Alzheimer's disease and cognitive disorders for use in combination with the compounds of the present application include donepezil, tacrine, revastigraine, 5HT6 receptor antagonists, gamma secretase inhibitors, beta secretase inhibitors, SK channel blockers, Maxi-K blockers, and KCNQs blockers.

The compounds described in the present application could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present application could be used in combination with agents used to treat erectile dysfunction. Examples of suitable treatment for erectile dysfunction include sildenafil (Viagra), vardenafil (Levitra) and tadalafil (Cialis). Other compounds that could be used in combination for erectile dysfunction include yohimbine, phentolamine and papaverine.

The compounds described in the present application could be used in combination with suitable anti-inflammatory agents. Examples of suitable anti-inflammatory agents for use in combination with the compounds of the present application include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®, Arcoxia®, and Bextra®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1 inhibitor, tumor necrosis factor (TNF) antagonists (e.g., infliximab, OR1384, including TNF-alpha inhibitors, such as tenidap, anti-TNF antibodies or soluble TNF receptor such as etanercept (Enbrel®), Remicade®, rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with $5HT_{2C}$ modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", J. Immunol. Methods (Netherlands), 188(1), pp. 1-7 (Dec. 15, 1995); Hollenbaugh, D., et al, "The Human T Cell Antigen Gp39, A Member of the TNF Gene Family, Is a Ligand for the CD40 Receptor: Expression of a Soluble Form of Gp39 with B Cell Co-Stimulatory Activity", EMBO J (England), 11(12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," New England J. of Medicine, 337(3), pp. 141-147 (1997).

The above other therapeutic agents, when employed in combination with the compounds of the present application, may be used, for example, in those amounts indicated in the Physicians' Desk Reference (PDR) or as otherwise determined by one of ordinary skill in the art.

The compounds of formula I of the application can be administered orally or parenterally, such as subcutaneously or intravenously, as well as by nasal application, transdermally, rectally or sublingually to various mammalian species known to be subject to such maladies, e.g., humans, in an effective amount within the dosage range of about 0.2 to 1000 mg, preferably from about 1 to 100 mg in a regimen of single, two or four divided daily doses.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intracistemal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

PHARMACOLOGICAL ANALYSIS

The pharmacological analysis of each compound for either antagonism or agonism of $5-HT_{2A}$, $5-HT_{2B}$ and $5-HT_{2C}$ receptors consisted of in vitro and in vivo studies. In vitro analyses included $K_i$ determinations at $5-HT_{2A}$, $5-HT_{2B}$ and $5-HT_{2C}$ receptors and an assessment of functional (i.e., agonism or antagonism) activity at each receptor class by IP3 hydrolysis assays. Additional receptor assays were conducted to evaluate receptor specificity of $5-HT_{2C}$ receptors over monoamine and nuisance receptors (e.g. histamine, dopamine, and muscarinic). A compound is considered active as a $5-HT_2$ agonist if it has an $EC_{50}$ value or a $K_i$ value of less than about 50 micromolar; preferably less than about 1.0 micromolar; more preferably less than about 0.1 micromolar. Using the assays disclosed herein, compounds of the present application have been shown to have an $EC_{50}$ value of less than about 50 micromolar for $5-HT_2$ agonism.

In vivo assays assessed compound activity in a variety of behavioral paradigms including acute and chronic feeding models, anxiety and depression models (learned-helplessness, elevated plus maze, Geller-Siefter, conditioned taste aversion, taste reactivity, satiety sequence). In aggregate, these models reflect activity as a $5-HT_{2C}$ agonist (feeding models, anxiety models, depression models) and provide some indication as to bioavailability, metabolism and pharmacokinetics.

Radioligand binding experiments were conducted on recombinant human $5-HT_{2A}$, $5-HT_{2B}$, and $5-HT_{2C}$ receptors expressed in HEK293E cells. The affinities of compounds of the present application to bind at these receptors is determined by their capacity to compete for $[^{125}I]$-1-(2,5-dimethoxy-4-iodophenyl)-2-amino-propane (DOI) or $[^3H]$-lysergic acid diethylamide (LSD) binding at the $5-HT_{2A}$, $5-HT_{2B}$, or $5-HT_{2C}$ receptors. General references for binding assays include 1) Lucaites V L, Nelson D L, Wainscott D B, Baez M (1996) Receptor subtype and density determine the coupling repertoire of the $5-HT_2$ receptor subfamily. Life Sci., 59(13):1081-95. Glennon R A, Seggel M R, Soine W H, Herrick-Davis K, Lyon R A, Titeler M (1988) $[^{125}I]$-1-(2,5-dimethoxy-4-iodophenyl)-2-amino-propane: an iodinated radioligand that specifically labels the agonist high-affinity state of $5-HT_2$ serotonin receptors. J Med. Chem. (1988) 31(1):5-7 and 3 Leonhardt S, Gorospe E, Hoffman B J, Teitler M (1992) Molecular pharmacological differences in the interaction of serotonin with 5-hydroxytryptamine 1C and 5-hydroxytryptamine 2 receptors. Mol Pharmacol., 42(2):328-35.

The functional properties of compounds (efficacy and potency) were determined in whole cells expressing $5-HT_{2A}$, $5-HT_{2B}$, or $5-HT_{2C}$ receptors by assessing their ability to stimulate or inhibit receptor-mediated phosphoinositols hydrolysis and/or intracellular calcium release. The procedures used are described below.

IN VITRO BINDING ASSAYS

Stable Expression of $5-HT_{2A}$, $5-HT_{2B}$ and $5-HT_{2C}$ Receptors in HEK293E Cells Stable cell lines were generated by transfecting 293EBNA cells with plasmids containing human $5-HT_{2A}$, $5-HT_{2B}$, or $5-HT_{2C}$ receptor (INI, INV, VNV or VGV RNA-edited isoforms) cDNA using calcium phosphate. These plasmids also contained the cytomegalovirus (CMV) immediate early promoter to drive receptor expression and EBV oriP for their maintenance as an extrachromosomal element, and the hph gene from E. Coli to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The $5-HT_{2A}$ cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately $1\times10^8$ cells) expressing the $5-HT_{2A}$, $5-HT_{2B}$ or $5-HT_{2C}$ receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT$_{2A}$, 5-HT$_{2B}$ and 5-HT$_{2C}$ Receptors Radioligand binding studies were conducted to determine the binding affinities (Ki values) of compounds for the human recombinant 5-HT$_{2A}$, 5-HT$_{2B}$, and 5-HT$_{2C}$ receptors (Fitzgerald et al., 1999). Assays were conducted in disposable polypropylene 96-well plates (Costar Corp., Cambridge, Mass.) and were initiated by the addition of 5-HT$_{2A}$, 5-HT$_{2B}$, or 5-HT$_{2C}$ membrane homogenate in tissue buffer (10-30 (g/well) to assay buffer (50 mM Tris HCl, 0.5 mM EDTA, 10 mM pargyline, 10 mM MgSO$_4$, 0.05% ascorbic acid, pH 7.5) containing [$^{125}$I]DOI for the 5-HT$_{2A}$ and 5-HT$_{2C}$ receptors (0.3-0.5 nM, final) or [$^3$H]LSD (1-2.0 nM, final) for the 5-HT$_{2B}$ receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (Packard cell harvester; Perkin-Elmer) over GFB glass-fiber filters that had been pre-soaked in 0.3% polyethyleneimine. Filters were washed in ice-cold 50 mM Tris HCl buffer (pH 7.5) and then counted on a Top Count (Packard).

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT$_{2A}$, 5-HT$_{2B}$, or 5-HT$_{2C}$ receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/mL hygromycin B, and 250 (g/mL G418. Following a 24-48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16-18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Calcium Fluorescence Studies

The ability of newly synthesized compounds to stimulate calcium fluorescence was monitored in whole cells using a protocol described previously (Fitzgerald et al., 1999). HEK293E cells expressing the human 5-HT$_{2C}$, or 5-HT$_{2B}$ receptor were lifted with 0.5 mM EDTA and plated at a density of 50,000/well onto poly-D-lysine-coated 96-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 µg/mL hygromycin B, and 250 µg/mL G418. Following a 24 hr period, the cell plates were removed from the incubator and an equal volume of Loading Buffer (Hanks BSS with 200 mM HEPES, pH 5.98) containing the calcium dye reagent (Fluo-3) is added to each well (100 µL per well for 96-well plates and then incubated for 1 hour at 37 C. Following the dye loading of the cells he plates are transferred to the FLIPR. Test compounds are added to the plate as a concentration response curve and the changes in fluorescence units due to calcium influx are monitored for a period of three seconds.

Data Analyses

The equilibrium apparent dissociation constants (Ki's) from the competition experiments were calculated using an iterative nonlinear regression curve-fitting program (Excelfit and TA Activity Base). For the PI hydrolysis and FLIPR experiments, EC50's were calculated using a one-site 'pseudo' Hill model: $y=((Rmax-Rmin)/(1+R/EC50)nH))+Rmax$ where R=response (GraphPad Prism; San Diego, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

Efficacy Models to Evaluate Food Consumption and Weight Loss

Acute overnight feeding assay. Compounds are assessed to for their ability to reduce food consumption during the dark cycle, which is the most active period of feeding in the rat. Fischer 344 rats are trained on a fixed ratio three (FR3) response paradigm which requires them to press a bar 3 consecutive times in order to obtain a food pellet. The number of bar presses occurring throughout the dark cycle can be monitored electronically as a measure of food intake by the animal. Rats are dosed orally or intraperitoneally with test compound 30 minutes prior to the onset of the dark cycle. The treated animals are then placed in individual operant boxes for 15 hours (12 hrs of dark cycle and the first three hours of the light cycle). Food intake in compound treated animals is compared to that of vehicle treated animals in order to determine percent reductions in food intake. Simultaneous measurements of water intake and locomotor activity are also measured during the period to assess for potential adverse effects.

Chronic Feeding Assay

Compounds are assessed for their long term impact on food intake and body weight in a three to fourteen week chronic treatment paradigm in Sprague-Dawley rats (starting weight ~450 g). Male Sprague-Dawley rats are pre-handled for one week prior to the onset of dosing during which time they are also assessed for food intake behavior. Rats are then assigned to treatment groups. Rats are dosed with vehicle or compound by oral gavage. The food intake and body weights are cumulatively assessed at the end of each treatment week and compared to vehicle treated animals. In some studies food intake is measured daily in order to assess the impact of reduced food consumption on pair-fed animals. At the end of the study period the animals are assessed for changes in body composition utilizing DEXA and are then sacrificed in order to examine changes in various blood plasma parameters.

REFERENCES

Arnt, J. Acta Pharmacol. et Toxicol. 1982: 51, 321-329.
Berridge M. J., Downes P. C., Hanley M. R. (1982) Lithium amplifies agonist-dependent phosphotidyinositol response in brain and salivary glands. Biochem. J., 206, 587-595.

Costall, B and Naylor, R J. Psychopharmacology. 1975: 43, 69-74.

Egan C. T., Herrick-Davis K., Miller K., Glennon R. A., and Teitler M. (1998) Agonist activity of LSD and lisuride at cloned 5-HT$_{2A}$ and 5-HT$_{2C}$ receptors. Psychopharmacology, 136, 409-414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT$_{2A}$ and 5-HT$_{2C}$ receptors: evidence favoring the ternary complex and two-state models of agonist action. J. Neurochem., 72, 2127-2134.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301-308.

DOSAGE AND FORMULATIONS

The serotonin agonist and serotonin antagonist compounds of this application can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT$_2$ receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form. Further, they may also be administered by internasal delivery, transdermal delivery and suppository or depot delivery all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.01 to about 30 mg/kg. Advantageously, compounds of the present application may be administered in a single daily dose, or the total daily dosage may be administered in divided doses of two, three, or four times daily.

Dosage forms of compositions suitable for administration contain from about 0.5 mg to about 100 mg of active ingredient per unit. In these pharmaceutical compositions the active ingredient will ordinarily be present in an amount of about 0.5-95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this application can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

EXAMPLES

Example 1

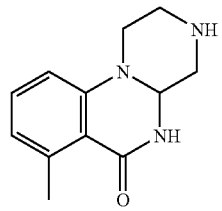

7-Methyl-1,2,3,4,4a,5-hexahydropyrazino[1,2-a]quinazolin-6-one

Part A. 2-Methyl-6-nitrobenzamide

To a solution of 2-methyl-6-nitrobenzoic acid (10.0 g, 55.2 mmol) and oxalyl chloride (5.78 mL, 66.3 mmol) in dichloromethane (100 mL) was added DMF (5 drops). The reaction mixture stirred at RT for 2 hours and then concentrated to about 25 mL. The mixture was slowly poured into a cold solution (0° C.) of 7 N ammonia in methanol (500 mL). The reaction mixture was stirred at RT for 30 min, concentrated and the residue was dissolved in ethyl acetate (150 mL). The ethyl acetate solution was washed with with saturated sodium bicarbonate (2×200 mL), dried over sodium sulfate and concentrated to give the title compound (9.5 g, 67%) as a light brown solid.

Part B. 2-Amino-6-methylbenzamide

A mixture of the compound from step A (4.0 g, 22.21 mmol) and 10% palladium on activated carbon (400 mg wet, Aldrich) in methanol (200 mL) was shaken (using a Parr shaker) under 50 PSI hydrogen for 1.5 hr. The reaction mixture was filtered and the filtrate was concentrated to give the title compound (3.1 g, 95%) as a brown solid.

Part C. t-Butyl (5-methyl-4-oxo-1,2,3,4-tetrahydroquinazolin-2-yl)methylcarbamate A mixture of the compound from step B (895 mg, 5.96 mmol), t-butyl (N-2-oxoethyl)carbamate (1.00 g, 6.28 mmol) and p-toluenesulfonic acid monohydrate (113 mg, 0.59 mol) in toluene (50 mL) was heated under reflux for 6 hours using a Dean-Stark trap. The reaction mixture was cooled to room temperature, followed by the addition of triethylamine (0.838 mL, 5.96 mmol) and 1.0M di-t-butyl dicarbonate (5.96 mL, 5.96 mmol). The reaction mixture was stirred at room temperature for 30 min, concentrated, and the crude product was purified by ISCO flash chromatography (silica gel/hexane-ethyl acetate 100:0 to 0:100 gradient) to afford the title compound 700 mg (40% yield) as a brown gum.

Part D. t-Butyl (1-allyl-5-methyl-4-oxo-1,2,3,4-tetrahydroquinazolin-2-yl)methylcarbamate A mixture of the compound from step C (3.0 g, 10.3 mmol), $K_2CO_3$ (2.84 g, 20.6 mmol), allyl bromide (1.34 mL, 15.5 mmol) and N,N-dimethylacetamide (40 mL) was heated at 140° C. for 2 hours in a sealed tube. The reaction mixture cooled to room temperature, diluted with ethyl acetate (100 mL) and was washed with a solution of aqueous saturated sodium bicarbonate (3×100 mL). The ethyl acetate layer was dried over sodium sulfate and concentrated. The crude product was purified by ISCO flash chromatography (silica gel/hexane-ethyl acetate 100:0 to 0:100 gradient) to afford the title compound 2.0 g (58% yield) as a yellow solid.

Part E. t-Butyl 7-methyl-6-oxo-1,2,4,4a,5,6-hexahydropyrazino[1,2-a]quinazoline-3-carboxylate To a mixture of the compound from step D (870 mg, 2.63 mmol) and sodium periodate (1.70 g, 7.88 mmol) in THF (40 mL) and water (40 mL) was added a solution of aqueous 2% osmium tetroxide (0.5 mL). The reaction mixture was stirred at room temperature for 3 h, diluted with ethyl acetate (100 mL) and washed with water (100 mL). The ethyl acetate layer was dried over sodium sulfate, concentrated and the crude product was dissolved in dichloromethane (50 mL) followed by the addition of triethylsilane (3 mL) and TFA-dichloromethane (10:90, 20 mL). The reaction mixture stirred at room temperature for 3 h and concentrated. The resulting dark brown gum was dissolved in dichloromethane followed by the addition of triethylamine (5 mL) and 1.0M di-t-butyl dicarbonate (2.63 mL, 2.63 mmol). The reaction mixture was stirred at room temperature for 1 h, concentrated and the crude product was purified by ISCO flash chromatography (silica gel/hexane-ethyl acetate 100:0 to 0:100 gradient) to afford the title compound 1.70 g (89% yield) as a brown solid.

Part F. (±)-7-Methyl-1,2,3,4,4a,5-hexahydropyrazino[1,2-a]quinazolin-6-one

A solution of the compound from step E (400 mg, 1.26 mmol) in dichloromethane (5 mL) and TFA (5 mL) was stirred at room temperature for 1 h. The reaction mixture was concentrated and the crude product was dissolved in methanol (5 mL) and loaded onto benzene sulfonic acid ion-exchange column. The column was washed with methanol (50 mL) and the product was eluted with a solution of 7 N ammonia in methanol (50 mL) to give the title compound, 259 mg (95%) as a light brown solid.

Part G. (+)-7-Methyl-1,2,3,4,4a,5-hexahydropyrazino[1,2-a]quinazolin-6-one (Enantiomer A)

The racemic mixture from part F was subjected to chiral chromatography (chiralcel OJ column (50×500 mm)/hexanes-ethanol-methanol-triethylamine 80:10:10:0.3) to give the title compound as the faster moving enantiomer. This material was treated in dichloromethane with a solution of HCl in ether to afford the corresponding HCl salt (off-white solid). 1H NMR(CD3OD, 400 MHz) δ 2.61(s, 3H), 3.07(t, 1H), 3.32(m, 2H), 3.48(d, 2H), 3.97(d, 1H), 4.68(d, 1H), 6.87(m, 2H), 7.35(t, 1H); $[\alpha]_D$+144° (c=1, MeOH); MS 218 $[M+H]^+$.

Part H. (−)-7-Methyl-1,2,3,4,4a,5-hexahydropyrazino[1,2-a]quinazolin-6-one (Enantiomer B)

This compound was prepared as described in part G (slower moving component on the chiralcel OJ column). $[\alpha]_D$−145° (c=1, MeOH); MS 218 $[M+H]^+$.

Example 2

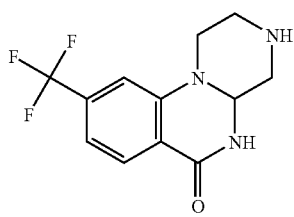

9-(Trifluoromethyl)-1,2,3,4,4a,5-hexahydropyrazino[1,2-a]quinazolin-6-one

Part A. 2-(Allylamino)4-(trifluoromethyl)benzamide

A mixture of 2-fluoro-4-trifluoromethylbenzamide (5.60 g, 27.05 mmol.), $K_2CO_3$ (11.2 g, 81.16 mmol), allylamine (7.71 g, 135.26 mmol) and dimethylacetamide (50 mL) was heated at 140° C. for 18 hours. The reaction mixture was cooled to room temperature, diluted with ethyl acetate (100 mL) and washed with a solution of aqueous saturated sodium bicarbonate (3×100 mL). The ethyl acetate layer was dried over sodium sulfate and concentrated to give the title compound (6.5 g, 98% yield) as a brown solid.

Part B. t-Butyl (1-allyl-4-oxo-7-(trifluoromethyl)-1,2,3,4-tetrahydroquinazolin-2-yl)methylcarbamate This compound was prepared as described for the part C compound of Example 1 (brown foam, 43% yield).

Part C. t-Butyl 6-oxo-9-(trifluoromethyl)-1,2,4,4a,5,6-hexahydropyrazino[1,2-a]quinazoline-3-carboxylate This compound was prepared in a manner similar to that described for the part E compound of Example 1 (white solid, 74%).

Part D. 9-(Trifluoromethyl)-1,2,3,4,4a,5-hexahydropyrazino[1,2-a]quinazolin-6-one This compound was prepared in a manner similar to that described for the part F compound of Example 1 (white solid, 88%).

Part E. 9-(Trifluoromethyl)-1,2,3,4,4a,5-hexahydropyrazino[1,2-a]quinazolin-6-one (Enantiomer A)

The racemic mixture from part D was subjected to chiral chromatography (chiralcel OD column/hexanes-ethanol-methanol-triethylamine 75:12.5:12.5:0.3) to give the title compound as the faster moving enantiomer (white solid). 1H NMR (CD$_3$OD, 500 MHz) δ 2.34(s, 3H), 2.76(m, 2H), 2.90(tt, 1H), 3.12(m, 2H), 3.65(d, 1H), 4.38(dd, 1H), 6.75(d, 2H), 7.68(d, 1H); MS 272 [M+H]$^+$.

Part F. 9-(Trifluoromethyl)-1,2,3,4,4a,5-hexahydropyrazino[1,2-a]quinazolin-6-one (Enantiomer B)

This compound was prepared as described above in part E (slower moving component on the chiralcel OD column). MS 272 [M+H]$^+$.

Example 3

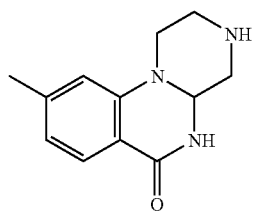

9-Methyl-1,2,3,4,4a,5-hexahydropyrazino[1,2-a]quinazolin-6-one

Part A. t-Butyl 9-bromo-6-oxo-1,2,4,4a,5,6-hexahydropyrazino[1,2-a]quinazoline-3-carboxylate This compound was prepared in a manner similar to that described for the part E compound of Example 1 (brown solid, 67% yield).

Part B. t-Butyl 9-methyl-6-oxo-1,2,4,4a,5,6-hexahydropyrazino[1,2-a]quinazoline-3-carboxylate A mixture of the product from part A (50 mg, 0.13 mmol), lithium chloride (15 mg, 0.35 mmol), tetramethyltin (55 μl, 0.39 mmol) and tetrakis(triphenylphosphine)palladium(0) (1 mg, 0.86 μmol) in degassed DMF (1.5 mL) was heated at 90° C. under nitrogen for 18 h. The mixture was diluted with ethyl acetate (20 mL), washed with a solution of aqueous saturated sodium bicarbonate (3×20 mL), dried over sodium sulfate and concentrated. The crude product was purified was purified by ISCO flash chromatography (silica gel/hexane-ethyl acetate 100:0 to 0:100 gradient) to afford the title compound 35 mg (84% yield) as a white solid.

Part C. 9-Methyl-1,2,3,4,4a,5-hexahydropyrazino[1,2-a]quinazolin-6-one

This compound was prepared as described for the part F compound of Example 1 (white solid, 17.4 mg, 73% yield); $^1$H NMR(CD3OD, 500 MHz) δ 2.34 (s, 1H), 2.71 (t, 1H), 2.78 (t, 1H), 2.90 (t, 1H), 3.10 (m, 2H), 3.65 (d, 1H), 4.38 (d, 1H), 6.75 (s, 2H), 7.70 (d, 1H); MS 218 [M+H]$^+$.

Example 4

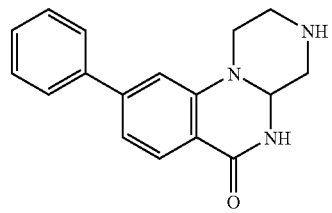

9-Phenyl-1,2,3,4,4a,5-hexahydropyrazino[1,2-a]quinazolin-6-one

Part A. t-Butyl 6-oxo-9-phenyl-1,2,4,4a,5,6-hexahydropyrazino[1,2-a]quinazoline-3-carboxylate A mixture of the part A compound from Example 3 (100 mg, 0.26 mmol), phenyl boronic acid (48 mg, 0.39 mmol), a solution of aqueous 2.0 M sodium bicarbonate (380 μl, 0.76 mmol) and tetrakis(triphenylphosphine) palladium(0) (1 mg, 0.86 μmol) in degassed DME (1.5 mL) was heated at 90° C. for 18 h under nitrogen. The mixture was diluted with ethyl acetate (20 mL), washed with a solution of aqueous saturated sodium bicarbonate (3×20 mL), dried over sodium sulfate and concentrated. The crude product was purified by ISCO flash chromatography (silica gel/hexane-ethyl acetate 100:0 to 0:100 gradient) to afford the title compound as a white solid (45 mg, 45% yield).

Part B. 9-Phenyl-1,2,3,4,4a,5-hexahydropyrazino[1,2-a]quinazolin-6-one

This compound was prepared as described for the part F compound of Example 1 (brown solid, 95% yield); 1H NMR(CD3OD, 500 MHz) δ 2.83(q, 2H), 2.94(t, 1H), 3.16 (m, 2H), 3.80(d, 1H), 4.48(dd, 1H), 7.11(s, 1H), 7.17(d, 1H), 7.37(t, 1H), 7.44(t, 2H), 7.63(d, 2H), 7.87(d, 1H); MS 280 [M+H]+.

Example 5

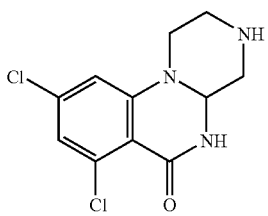

7,9-Dichloro-1,2,3,4,4a,5-hexahydropyrazino[1,2-a]quinazolin-6-one

Part A. 2,4-Dichloro-6-fluorobenzoic acid

A solution of 2.5 M n-butyllithium in hexane (8.72 mL, 21.8 mmol) was added to anhydrous THF (100 mL) at −78° C. under nitrogen with stirring, followed by the addition of 1.0 M potassium t-butyloxide in THF (21.81 mL, 21.8 mmol). The reaction mixture was stirred at −78° C. for 30 min, then 3,5-dichlorofluorobenzene (3.0 g, 18.2 mmol) was added over 10 min and the mixture was stirred at −78° C. for 40 minutes. Carbon dioxide gas was then bubbled into the reaction mixture for 10 min The reaction mixture was allowed to come to RT, diluted with ether (100 mL), extracted with a solution of aqueous 1.0 M sodium hydroxide (2×50 mL). The combined sodium hydroxide extract was washed with ether (100 mL). The sodium hydroxide layer was then acidified to pH 3 with a solution of aqueous concentrated HCl, extracted with ethyl acetate (2×50 mL). The combined ethyl acetate layers were dried over sodium sulfate and concentrated. The crude product was purified by ISCO flash chromatography (silica gel/hexane-ethyl acetate 100:0 to 0:100 gradient) to afford the title compound as a brown solid (1.34 g, 35% yield).

Part B. 2,4-dichloro-6-fluorobenzamide

To a solution of the product from step A (1.34 g, 6.44 mmol) in dichloromethane (30 mL) was sequentially added oxalyl chloride (817 μl, 6.99 mmol) and DMF (2 drops). The reaction mixture stirred at RT for 1 h, concentrated, the residue was dissolved in dichloromethane (10 mL) and slowly added to an ice cold solution of 7 N ammonia in methanol (150 mL). The reaction mixture was stirred at RT for 1 h, concentrated, dissolved in ethyl acetate and washed with water. The organic layer was dried over sodium sulfate and concentrated to give the title compound as a brown solid (1.22 g, 92% yield).

Part C. 7,9-Dichloro-1,2,3,4,4a,5-hexahydropyrazino[1,2-a]quinazolin-6-one

This compound was prepared from the product of step B from above by using the the sequence of steps described for Example 2. 1H NMR(CD3OD, 500 MHz) δ 2.17(t, 1H), 2.69(m, 2H), 2.85(m, 1H), 3.12(m, 1H), 3.53(d, 1H), 4.30(d, 1H), 6.90(s, 1H), 6.94(s, 1H); MS 272 [M+H]+.

Example 6

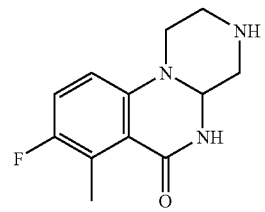

8-Fluoro-7-methyl-1,2,3,4,4a,5-hexahydropyrazino[1,2-a]quinazolin-6-one

Part A. t-Butyl 7-chloro-8-fluoro-6-oxo-1,2,4,4a,5,6-hexahydropyrazino[1,2-a]quinazoline-3-carboxylate This compound was prepared in a manner similar to that described for the part C compound of Example 2.

Part B. t-Butyl 8-fluoro-7-methyl-6-oxo-1,2,4,4a,5,6-hexahydropyrazino[1,2-a]quinazoline-3-carboxylate A mixture of the product from part A (140 mg, 0.39 mmol), potassium carbonate (163 mg, 1.18 mmol), trimethylboroxane (61 μl, 0.43 mmol) and tetrakis(triphenylphosphine) palladium(0) (45 mg, 0.039 mmol) in 10% degassed aqueous dioxane (5 mL) was heated under nitrogen for 5 h. The mixture was diluted with ethyl acetate (30 mL), aqueous saturated sodium bicarbonate (2×20 mL), dried over sodium sulfate and concentrated. The crude product was purified was purified by ISCO flash chromatography (silica gel/hexane-ethyl acetate 100:0 to 0:100 gradient) to afford the title compound 80 mg (61% yield) as a white solid.

Part C. 8-Fluoro-7-methyl-1,2,3,4,4a,5-hexahydropyrazino[1,2-a]quinazolin-6-one

This compound was prepared by using the procedure described in step F, Example 1. Light brown solid; 1H NMR(CD3OD, 500 MHz) δ 2.44(s, 3H), 2.97(t, 1H), 3.20 (m, 2H), 3.43(d, 2H), 3.77(d, 1H), 4.59(dd, 1H), 6.84(dd, 1H), 7.13(t, 1H); MS 236 [M+H]+.

Example 7

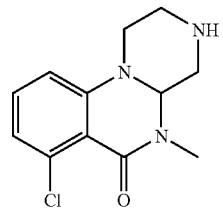

7-Chloro-5-methyl-1,2,3,4,4a,5-hexahydropyrazino[1,2-a]quinazolin-6-one

Part A. t-Butyl (5-chloro-4-oxo-1,2,3,4-tetrahydroquinazolin-2-yl)methylcarbamate A mixtre of 2-chloro-6-nitrobenzamide (0.3 g), iron powder (0.5 g) and t-butyl (N-2-oxoethyl)carbamate (1.0 g) in glacial acetic acid (5 mL) was heated at 50-55° C. for 2 h.

The mixture was concentrated and the residue was partitioned between sat. NaHCO₃ and EtOAc. The organic layer was dried (MgSO₄), concentrated, and the residue was subjected to flash chromatography (silica gel/heptane-EtOAc 100:0 to 20:80 gradient) to afford the title compound as an off-white solid (0.1 g).

Part B. t-Butyl (1-allyl-5-chloro-4-oxo-1,2,3,4-tetrahydroquinazolin-2-yl)methylcarbamate This compound was prepared as described for the part D compound of Example 1.

Part C. t-Butyl 7-chloro-6-oxo-1,2,4,4a,5,6-hexahydropyrazino[1,2-a]quinazoline-3-carboxylate This compound was prepared as described for the part E compound of Example 1.

Part D. 7-Chloro-5-methyl-1,2,3,4,4a,5-hexahydropyrazino[1,2-a]quinazolin-6-one

A mixure of the compound from part C (12 mg), 95% sodium hydride (3 mg) and methyl iodide (0.1 mL) in 1 mL DMF was stirred at RT for 0.5 h. The mixture was quenched with 0.1 mL water and concentrated to afford crude t-Butyl 7-chloro-5-methyl-6-oxo-1,2,4,4a,5,6-hexahydropyrazino[1,2-a]quinazoline-3-carboxylate. This was taken in 2:1 dichloromethane-TFA (3 mL), stirred at RT for 10 min, concentrated and the residue was stirred over powdered potassium carbonate for 0.5 h at RT in dichloromethane. The mixture was filtered, the filtrate was concentrated and the residue was subjected to flash chromatography (silica gel/methylene chloride-MeOH—NH₄OH 90:10:1) to afford the title compound as an off-white solid (7 mg).

Example 8

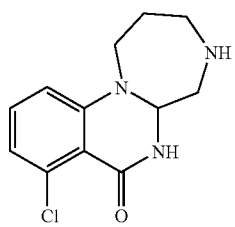

8-Chloro-2,3,4,5,5a,6-hexahydro-[1,4]diazepino[1,2-a]quinazolin-7(1H)-one

Part A. t-Butyl (5-chloro-1-(3-hydroxypropyl)4-oxo-1,2,3,4-tetrahydroquinazolin-2-yl)methylcarbamate Borane-methyl sulfide (3 mL) was added to a stirred solution of the compound from step B, Example 7 (0.15 g) in 5 mL ether at RT. The mixture was stirred at RT for 15 min, then poured into a mixture of 30% hydrogen peroxide (10 mL) and 1N aqueous NaOH (30 mL) at ca. 0° C. The mixture was stirred at RT for 30 min and diluted with EtOAc. The organic phase was dried (MgSO₄), concentrated and the residue was purified by flash chromatography (silica gel/EtOAc-MeOH-EtOH 100:0:0 to 95:2.5:2.5 gradient) to give the title compound as a pale gum (50 mg).

Part B. 8-Chloro-2,3,4,5,5a,6-hexahydro-[1,4]diazepino[1,2-a]quinazolin-7(1H)-one Dess-Martins periodinane (52 mg, 0.123 mmol) was added to a stirred solution of the compound from step A (45 mg, 0.123 mmol) in dichloromethane (3 mL) and the reaction mixture was stirred at RT for 1 h. The reaction mixture was diluted with dichloromethane, washed with sat. NaHCO₃, the organic layer was dried (MgSO₄) and concentrated to afford crude t-Butyl (5-chloro-4-oxo-1-(3-oxopropyl)-1,2,3,4-tetrahydroquinazolin-2-yl)methylcarbamate. This material was dissolved in dichloromethane (3 mL) follwed by the addition of TFA (1 mL) and triethylsilane (1 mL). The mixture was stirred at RT for 1.5 h, concentrated and the residue was subjected to preparative HPLC (C18 silica/water-MeOH-TFA 90:10:0.1 to 10:90:0.1) to afford 6 mg of the title compound. This material was further purified by prep TLC (silica gel/dichloromethane-MeOH—NH₄OH 90:10:1) to afford the title compound as an off-white solid (2.2 mg).

Example 9

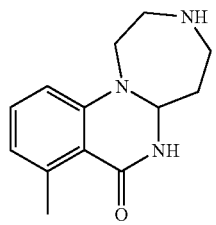

8-Methyl-2,3,4,5,5a,6-hexahydro-[1,4]diazepino[1,7-a]quinazolin-7(1H)-one

Part A. Benzyl 2-(5-methyl-4-oxo-1,2,3,4-tetrahydroquinazolin-2-yl)ethylcarbamate A mixture of the compound from step B in example 1 (1.06 g, 7.07 mmol), 3-benzyloxycarbonylamino-1-propanal (1.46 g, 7.07 mmol) and p-toluenesulfonic acid monohydrate (67 mg, 0.71 mmol) in 1,4-dioxane (18 mL) was stirred at room temperature for 1 hour. The reaction mixture was concentrated and the crude product was purified by flash chromatography (silica gel/hexane-ethyl acetate 100:0 to 0:100 gradient) to afford the title compound 1.66 g (69% yield) as a brown gum.

Part B. Benzyl 2-(1-allyl-5-methyl-4-oxo-1,2,3,4-tetrahydroquinazolin-2-yl)ethylcarbamate A mixture of the compound from step A (1.66 g, 4.89 mmol), K₂CO₃ (1.38 g, 9.79 mmol), allyl bromide (0.635 mL, 7.34 mmol) and N,N-dimethylacetamide (35 mL) was heated at 140° C. for 2 hours in a sealed tube. The reaction mixture cooled to room temperature, diluted with ethyl acetate (100 mL) and was washed with a solution of aqueous saturated sodium bicarbonate (3×100 mL). The ethyl acetate layer was dried over sodium sulfate and concentrated. The crude product was purified by flash chromatography (silica gel/hexane-ethyl acetate 100:0 to 0:100 gradient) to afford the title compound 800 mg (43% yield) as a brown solid.

Part C. Benzyl 8-methyl-7-oxo-1,2,5,5a,6,7-hexahydro-[1,4]diazepino[1,7-a]quinazoline-3(4H)-carboxylate To a mixture of the compound from step B (800 mg, 2.11 mmol) and sodium periodate (903 mg, 4.22 mmol) in THF (15 mL) and water (20 mL) was added a solution of aqueous 2% osmium tetroxide (0.2 mL). The reaction mixture was stirred at room temperature for 3 h, diluted with ethyl acetate (100 mL) and washed with water (100 mL). The ethyl acetate layer was dried over sodium sulfate, concentrated and the crude product was dissolved in dichloromethane (50 mL) followed by the addition of triethylsilane (2 mL) and TFA-dichloromethane (10:90, 20 mL). The reaction mixture was stirred at room temperature for 3 h and concentrated. The resulting dark brown gum was dissolved in dichloromethane followed by the addition of triethylamine (5 mL). The reaction mixture was stirred at room temperature for 5 minutes, concentrated and the crude product was purified by flash chromatography (silica gel/hexane-ethyl acetate 100:0 to 0:100 gradient) to afford the title compound 490 mg (63% yield) as a brown gum.

Part D. (±)-8-Methyl-2,3,4,5,5a,6-hexahydro-[1,4]diazepino[1,7-a]quinazolin-7(1H)-one A mixture of the compound from step C (300 mg, 0.82 mmol) and 10% palladium on activated carbon (100 mg wet, Aldrich) in methanol (20 mL) was shaken (using a Parr shaker) under 50 PSI hydrogen for 18 hr. The reaction mixture was filtered and the filtrate was concentrated to give the title compound (300 mg, 97%) as a brown solid.

Part E. 8-Methyl-2,3,4,5,5a,6-hexahydro-[1,4]diazepino[1,7-a]quinazolin-7(1H)-one (Enantiomer A)

The racemic mixture from part D was subjected to chiral chromatography (chiralcel OD column (50×500 mm)/hexanes-ethanol-methanol-triethylamine 80:10:10:0.3) to give the title compound as the faster moving enantiomer (white solid). 1H NMR(CD3OD, 400 MHz) δ 1.95(m, 1H), 2.01(m, 1H), 2.48(s, 3H), 2.74(m, 2H), 2.86(m, 1H), 3.07(m, 1H), 3.28(m, 1H), 3.78(m, 1H), 4.64(m, 1H), 6.51(d, 1H), 6.61(d, 1H), 7.13(t, 1H); MS 232 [M+H]+.

Part F. 8-Methyl-2,3,4,5,5a,6-hexahydro-[1,4]diazepino[1,7-a]quinazolin-7(1H)-one (Enantiomer B)

The racemic mixture from part D was subjected to chiral chromatography (chiralcel OD column (50×500 mm)/hexanes-ethanol-methanol-triethylamine 80:10:10:0.3) to give the title compound as the slower moving enantiomer (white solid). MS 232 [M+H]+.

Example 10

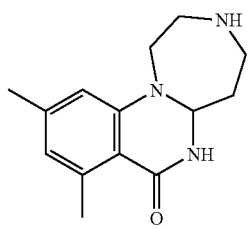

8,10-Dimethyl-2,3,4,5,5a,6-hexahydro-[1,4]diazepino[1,7-a]quinazolin-7(1H)-one

Part A. 2,4-Dibromo-6-fluorobenzoic acid

A solution of 1,3-dibromo-5-fluorobenzene 15.0 g, 59.07 mmol.) in anhydrous THF (300 mL) at −78° C. under nitrogen was added a solution of 2.0 M LDA in THF (35.44 mL, 70.89 mmol). The reaction mixture was stirred at −78° C. for 2 h. Carbon dioxide gas was then bubbled into the reaction mixture until the color of the reaction mixture turned clear. The reaction mixture was allowed to come to RT, diluted with ether (100 mL), extracted with a solution of aqueous 1.0 M sodium hydroxide (2×50 mL). The combined sodium hydroxide layer was washed with ether (100 mL). The sodium hydroxide layer was then acidified to pH 3 with a solution of concentrated HCl and extracted with ethyl acetate (2×50 mL). The combined ethyl acetate layer was dried over sodium sulfate and concentrated to give the title compound (14.14 g, 81% yield) as a brown solid.

Part B. 2,4-Dibromo-6-fluorobenzamide

To a solution of the product from step A (14.14 g, 47.77 mmol) in THF (50 mL) and dichloromethane (70 mL) was sequentially added oxalyl chloride (4.85 mL, 57.32 mmol) and DMF (10 drops). The reaction mixture stirred at RT for 1 h, concentrated, the residue was dissolved in dichloromethane (10 mL) and slowly added to an ice cold solution of 7N ammonia in methanol (350 mL). The reaction mixture was stirred at RT for 1 h, concentrated, dissolved in ethyl acetate and washed with water. The organic layer was dried over sodium sulfate and concentrated to give the title compound as a brown solid (11.74 g, 83% yield).

Part C. 2-(Allylamino)-4,6-dibromobenzamide

A mixture of the part B compound (8.0 g, 27.12 mmol.), K2CO3 (11.23 g, 81.35 mmol), allylamine (6.10 mL, 81.35 mmol) and dimethylacetamide (40 mL). was heated at 140° C. for 18 h. The reaction mixture was cooled to room temperature, diluted with ethyl acetate (50 mL) and washed with a solution of aqueous saturated sodium bicarbonate (3×50 mL). The ethyl acetate layer was dried over sodium sulfate and concentrated to give the title compound (brown solid, 91%, 8.23 g yield).

Part D. tert-Butyl 2-(1-allyl-5,7-dibromo-4-oxo-1,2,3,4-tetrahydroquinazolin-2-yl)ethylcarbamate A mixture of the compound from step C (8.23 g, 24.79 mmol), tert-butyl 3,3-diethoxypropylcarbamate (7.35 g, 29.75 mmol) and p-toluenesulfonic acid monohydrate (1.41 mg, 7.43 mmol) in dioxane (20 m/L) was srirred at room temperature for 3.5 h. The reaction mixture was then treated with triethylamine (3.0 mL, 22.00 mmol), stirred at room temperature for 30 min., concentrated, and the crude product was purified by ISCO flash chromatography (silica gel/hexane-ethyl acetate 100:0 to 0:100 gradient) to afford the title compound 10.50 g (70% yield) as a brown solid.

Part E. tert-Butyl 8,10-dibromo-7-oxo-1,2,5,5a,6,7-hexahydro-[1,4]diazepino[1,7-a]quinazoline-3(4H)-carboxylate This compound was prepared as described for the part E compound of Example 1 (brown gum, 163%, 16.7 yield).

Part F. tert-Butyl 8,10-dimethyl-7-oxo-1,2,5,5a,6,7-hexahydro-[1,4]diazepino[1,7-a]quinazoline-3(4H)-carboxylate A mixture of the compound from step E (3.11 g, 6.57 mmol), and PdCl2(dppf)2 (161 mg, 0.197 mmol.) in anhydrous dioxane (15 mL) was added 1.0 M dimethylzinc in haptane (26.30 mL, 26.30 mmol). The reaction mixture was srirred at reflux temperature for 2 h. The reaction mixture was cooled to room temperature, diluted with ethyl acetate (100 mL) and washed with a solution of aqueous saturated sodium bicarbonate (3×100 mL). The ethyl acetate layer was dried over sodium sulfate and concentrated. The crude product was purified by ISCO flash chromatography (silica gel/hexane-ethyl acetate 100:0 to 0:100 gradient) to afford the title compound 1.05 mg (46% yield) as a white solid.

Part G. 8,10-Dimethyl-2,3,4,5,5a,6-hexahydro-[1,4]diazepino[1,7-a]quinazolin-7(1H)-one This compound was prepared as described for the part F compound of Example, 650 mg (87%) as a light brown solid.

Part H. 8,10-Dimethyl-2,3,4,5,5a,6-hexahydro-[1,4]diazepino[1,7-a]quinazolin-7(1H)-one (Enantiomer A)

The racemic mixture from part G (65 mg, 0.28 mmol.) was subjected to chiral chromatography (chiralcel AD column/hexanes-ethanol-methanol-triethylamine 75:12.5:12.5: 0.3) to give the title compound as the faster moving enantiomer 289.25 mg (white solid). 1H NMR (CD$_3$OD, 500 MHz) δ 2.03(m, 1H), 2.12(m, 1H), 2.28(s, 3H), 2.57(s, 3H), 2.84(m, 2H), 2.94(m, 1H), 3.19(m, 1H), 3.36(m, 1H), 3.92 (m, 1H), 4.72(m, 1H), 6.46(s, 1H), 6.55(s, 1H); MS 246 [M+H]$^+$.

Part I. 8,10-Dimethyl-2,3,4,5,5a,6-hexahydro-[1,4]diazepino[1,7-a]quinazolin-7(1H)-one (Enantiomer B)

This compound was obtained by isolating the slower moving component from step H; MS 246 [M+H]$^+$.

Example 11

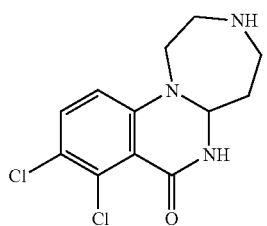

8,9-Dichloro-5a-methyl-2,3,4,5,5a,6-hexahydro-[1,4]diazepino[1,7-a]quinazolin-7(1H)-one Part A. tert-Butyl 2-(2-carbamoyl-3,4-dichlorophenylamino)ethylcarbamate A mixture of 2,3-dichloro-6-fluorobenzamide (4.0 g, 19.32 mmol.), K$_2$CO$_3$ (5.33 g, 38.64 mmol), and N-Boc-ethylenediamine (3.41 g, 21.25 mmol) and dimethylacetamide (50 mL). was heated at 140° C. for 18 h. The reaction mixture was cooled to room temperature, diluted with ethyl acetate (100 mL) and washed with a solution of aqueous saturated sodium bicarbonate (3×100 mL). The ethyl acetate layer was dried over sodium sulfate and concentrated to give the title compound (5.50 g, 82% yield) as a brown gum.

Part B. 2,3-Dichloro-6-(2-(n-(3-oxobutyl)tert-butyloxycarbonylamino)ethylamino)benzamide To a solution of the product from step A (540 mg, 1.55 mmol) in dichloromethane (5 mL) and trifluoroacetic acid (5 mL) was stirred at room temperature for 30 min. The reaction mixture was concentrated to give brown gum. The brown gum was taken in dioxane (5 mL) and treated with triethylamine (0.530 mL, 3.89 mmol) and methyl vinyl ketone (0.127 mL, 1.55 mmol.) at room temperature for 18 hour. A solution of 1.0 M di-t-butyl dicarbonate in THF (2 mL, 2.0 mmol) was added and the reaction mixture was stirred at room temperature for 30 minutes. The mixture was concentrated and the crude product was purified by ISCO flash chromatography (silica gel/hexane-ethyl acetate 100:0 to 0:100 gradient) to afford the title compound 280 mg (43% yield) as a brown gum.

Part C. tert-Butyl 8,9-dichloro-5a-methyl-7-oxo-1,2,5,5a,6,7-hexahydro-[1,4]diazepino[1,7-a]quinazoline-3(4H)-carboxylate A mixture of the compound from step B (280 mg, 0.67 mmol) and p-toluenesulfonic acid monohydrate (38 mg, 0.201 mmol) was heated with stirring in dioxane (10 mL) at 80° C. for 18 h. The reaction mixture was cooled to room temperature followed by the addition of triethylamine (0.838 mL, 5.96 mmol) and 1.0M di-t-butyl dicarbonate (2 mL, 2.0 mmol). The reaction mixture was stirred at room temperature for 30 min., concentrated, and the crude product was purified by ISCO flash chromatography (silica gel/hexane-ethyl acetate 100:0 to 0:100 gradient) to afford the title compound 219 mg (92% yield) as a white solid.

Part D. 8,9-Dichloro-5a-methyl-2,3,4,5,5a,6-hexahydro-[1,4]diazepino[1,7-a]quinazolin-7(1H)-one This compound was prepared as described for the part F compound of Example 1, 182 mg (81%) as a brown gum.

Part E. 8,9-Dichloro-5a-methyl-2,3,4,5,5a,6-hexahydro-[1,4]diazepino[1,7-a]quinazolin-7(1H)-one (enantiomer A)

The racemic mixture from part D (182 mg, 0.61 mmol) was subjected to chiral chromatography (chiralcel OD column/hexanes-ethanol-methanol-triethylamine 70:15:15:0.3) to give the title compound as the faster moving enantiomer 289.25 mg (white solid). 1H NMR (CD3OD, 500 MHz) δ 1.39(s, 3H), 2.19(m, 2H), 2.71(m, 1H), 3.08(m, 1H), 3.11(m, 2H), 3.30(m, 1H), 3.93(m, 1H), 6.91(d, 1H), 7.44(m, 1H); MS 300 [M+H]$^+$.

Part F. 8,9-Dichloro-5a-methyl-2,3,4,5,5a,6-hexahydro-[1,4]diazepino[1,7-a]quinazolin-7(1H)-one (Enantiomer B)

This compound was obtained by isolating the slower moving component from step E; MS 300 [M+H]$^+$.

Examples 12 to 168

The following compounds of Formula 1 were prepared by the procedures described above:

| Example No. | Structure | MS [M + H]$^+$ |
|---|---|---|
| 12 | 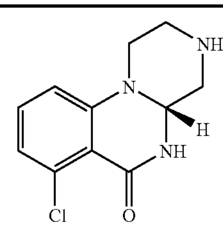 | 238 |
| 13 | 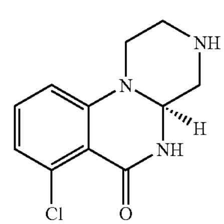 | 238 |
| 14 | 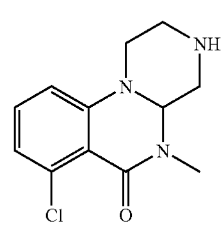 | 252 |

-continued
| Example No. | Structure | MS [M + H]+ |
|---|---|---|
| 15 | 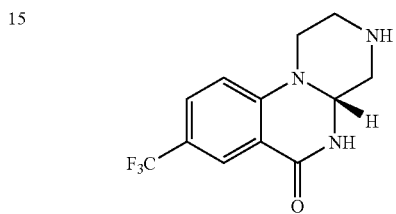 | 272 |
| 16 | 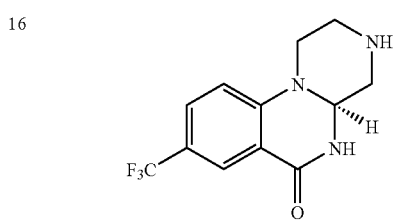 | 272 |
| 17 | 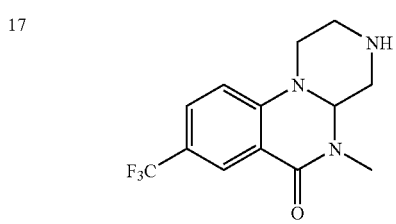 | 286 |
| 18 | 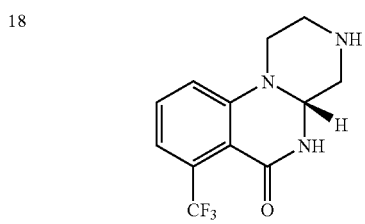 | 272 |
| 19 | 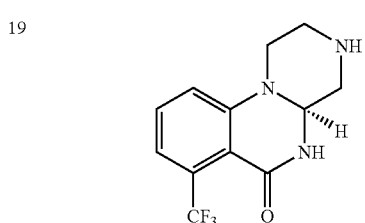 | 272 |
| 20 | 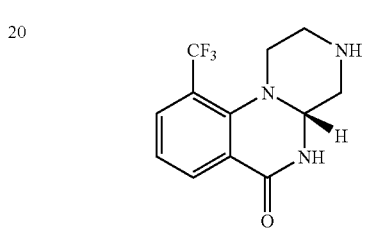 | 272 |
| 21 | 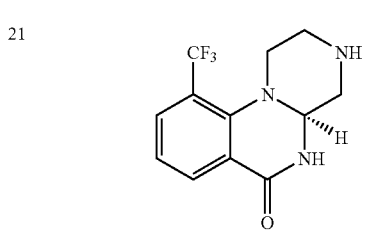 | 272 |
-continued
| Example No. | Structure | MS [M + H]+ |
|---|---|---|
| 22 | 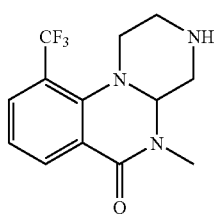 | 286 |
| 23 | 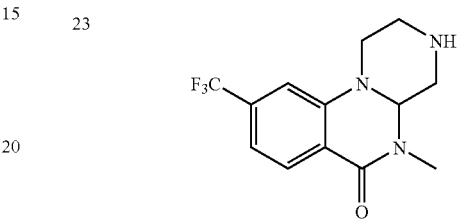 | 286 |
| 24 | 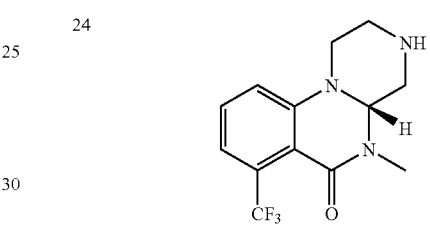 | 286 |
| 25 | 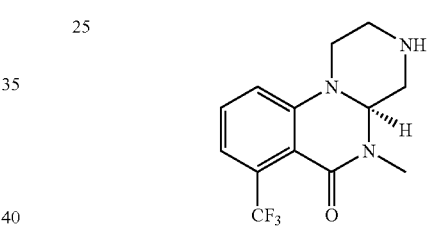 | 286 |
| 26 | 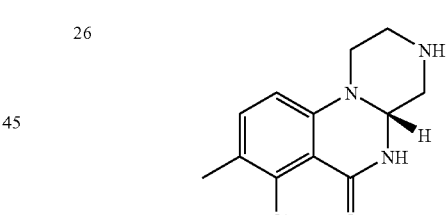 | 252 |
| 27 | 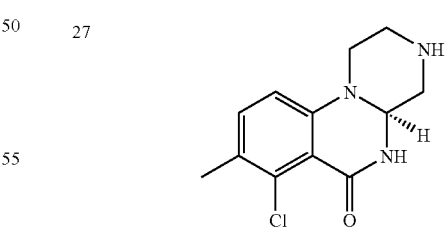 | 252 |
| 28 | 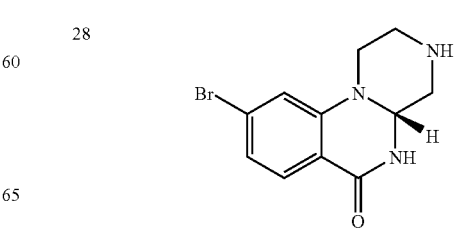 | 283 |

-continued
| Example No. | Structure | MS [M + H]+ |
|---|---|---|
| 29 | 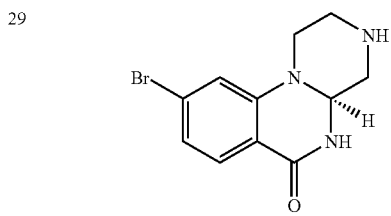 | 283 |
| 30 | 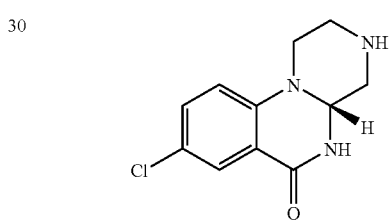 | 238 |
| 31 | 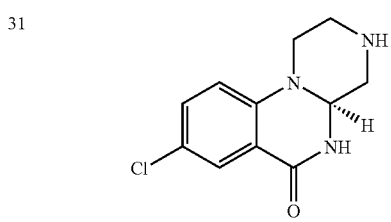 | 238 |
| 32 | 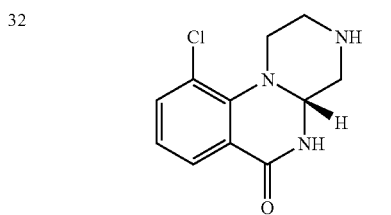 | 238 |
| 33 | 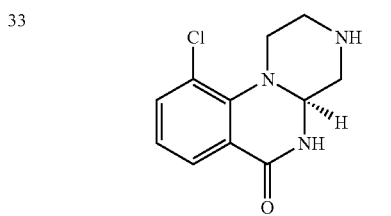 | 238 |
| 34 | 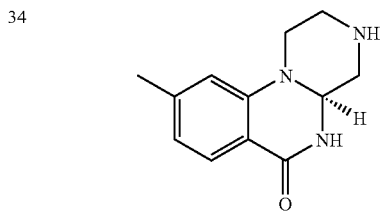 | 218 |
| 35 | 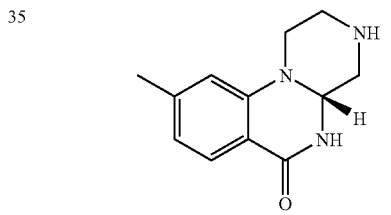 | 218 |
-continued
| Example No. | Structure | MS [M + H]+ |
|---|---|---|
| 36 | 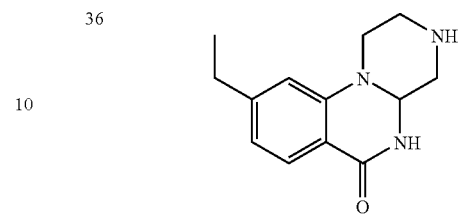 | 232 |
| 37 | 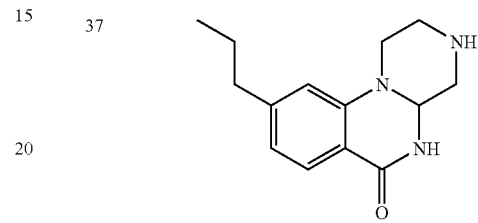 | 246 |
| 38 | 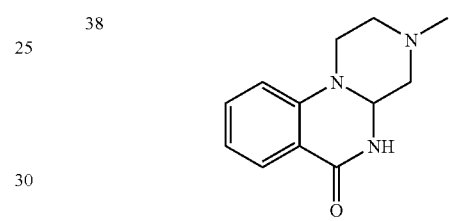 | 218 |
| 39 | 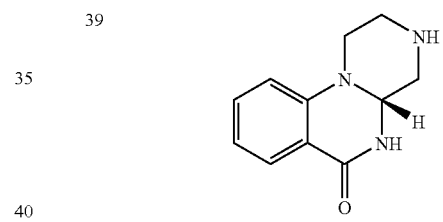 | 204 |
| 40 | 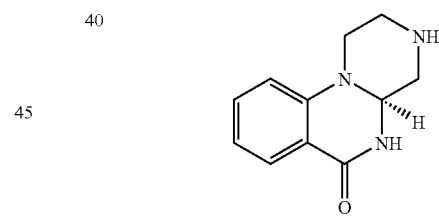 | 204 |
| 41 | 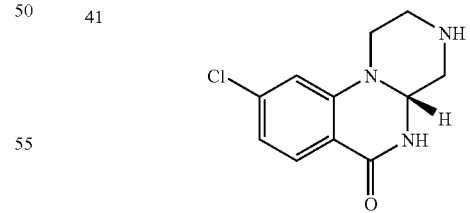 | 238 |
| 42 | 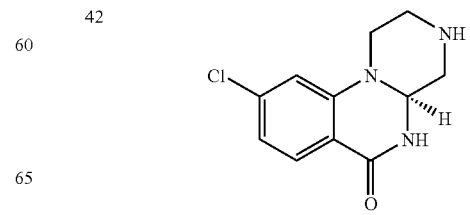 | 238 |

-continued
| Example No. | Structure | MS [M + H]+ |
|---|---|---|
| 43 | 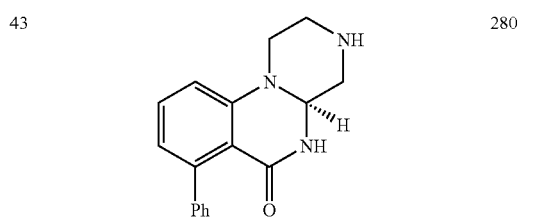 | 280 |
| 44 | 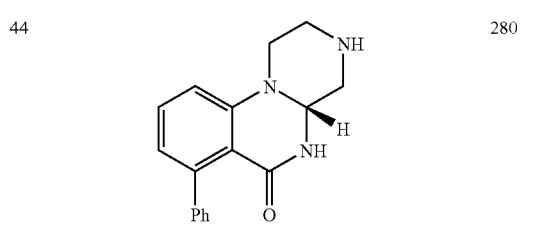 | 280 |
| 45 | 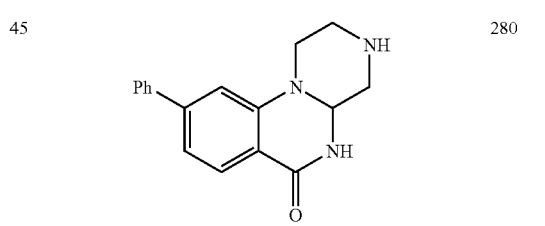 | 280 |
| 46 | 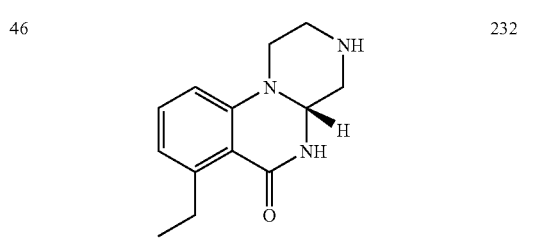 | 232 |
| 47 | 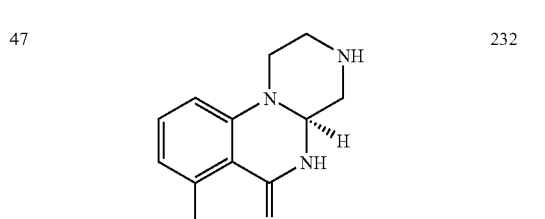 | 232 |
| 48 | 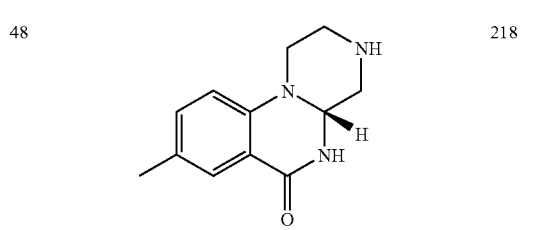 | 218 |
-continued
| Example No. | Structure | MS [M + H]+ |
|---|---|---|
| 49 | 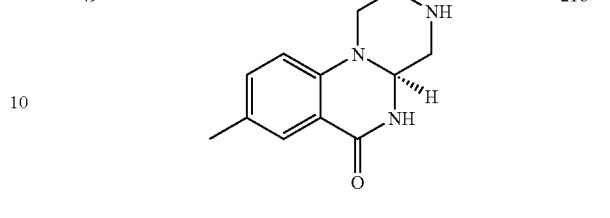 | 218 |
| 50 | 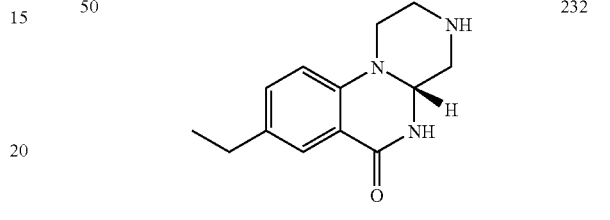 | 232 |
| 51 | 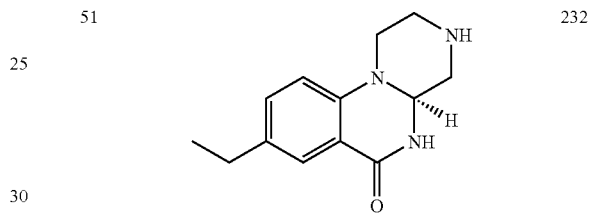 | 232 |
| 52 | 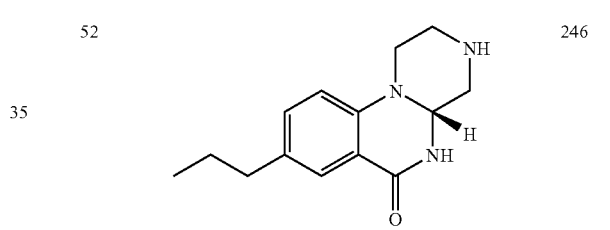 | 246 |
| 53 | 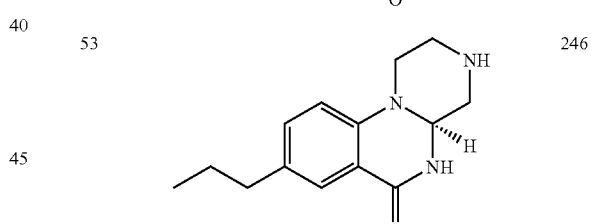 | 246 |
| 54 | 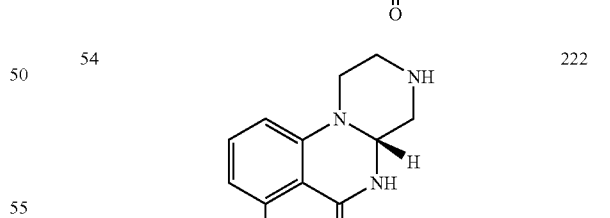 | 222 |
| 55 | 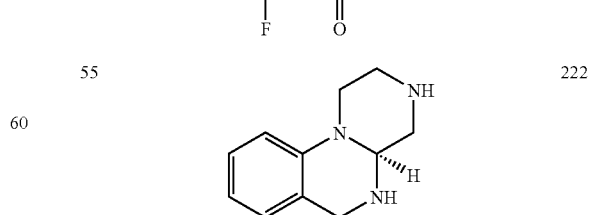 | 222 |

-continued
| Example No. | Structure | MS [M + H]+ |
|---|---|---|
| 56 | 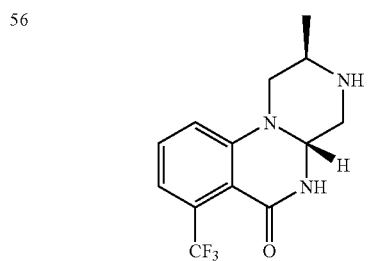 | 286 |
| 57 | 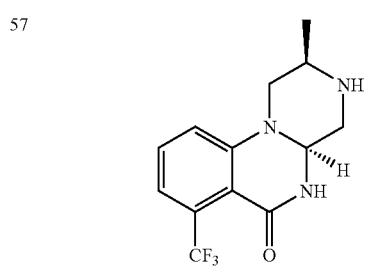 | 286 |
| 58 | 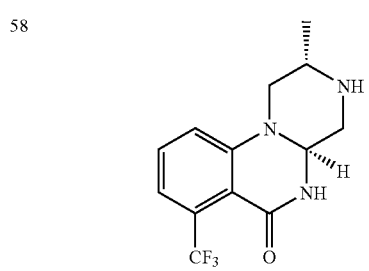 | 286 |
| 59 | 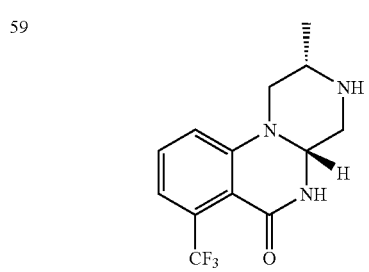 | 286 |
| 60 | 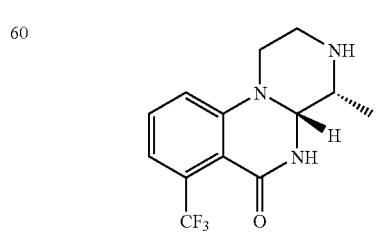 | 286 |
| 61 | 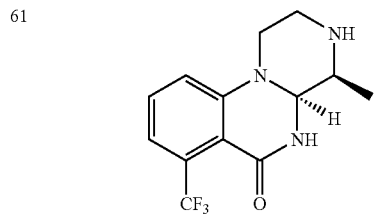 | 286 |
-continued
| Example No. | Structure | MS [M + H]+ |
|---|---|---|
| 62 | 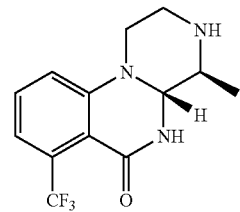 | 286 |
| 63 | 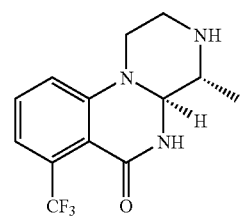 | 286 |
| 64 | 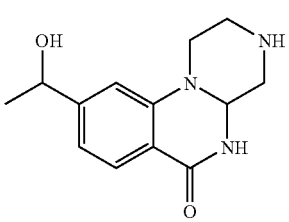 | 248 |
| 65 | 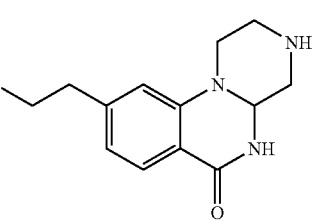 | 250 |
| 66 | 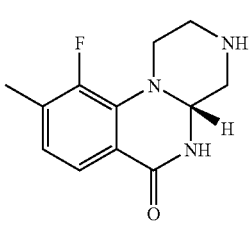 | 236 |
| 67 | 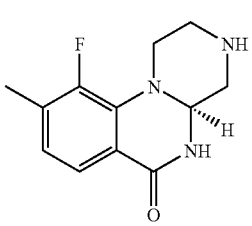 | 236 |
| 68 | 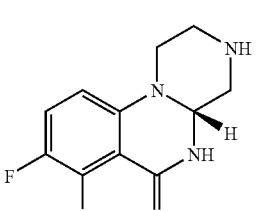 | 256 |

-continued

| Example No. | Structure | MS [M + H]+ |
|---|---|---|
| 69 | 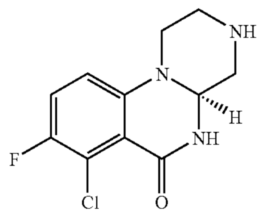 | 256 |
| 70 | 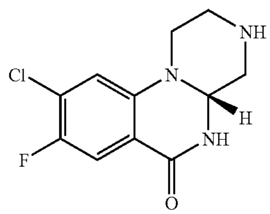 | 256 |
| 71 | 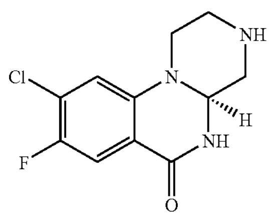 | 256 |
| 72 | 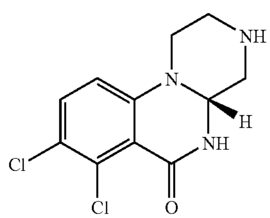 | 273 |
| 73 | 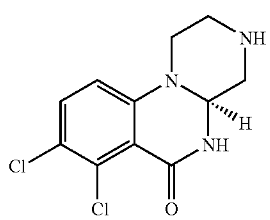 | 273 |
| 74 | 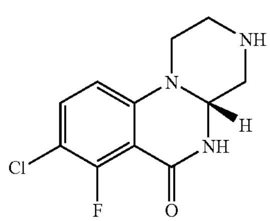 | 256 |
| 75 | 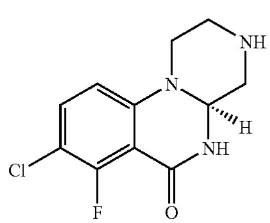 | 256 |
| 76 | | 273 |
| 77 | | 273 |
| 78 | | 236 |
| 79 | | 236 |
| 80 | | 286 |
| 81 | | 286 |

-continued
| Example No. | Structure | MS [M + H]+ |
|---|---|---|
| 82 | 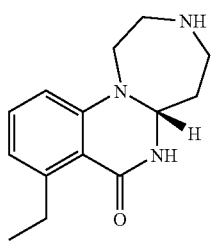 | 246 |
| 83 | 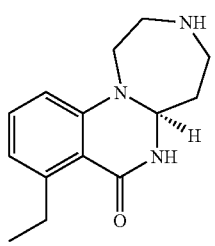 | 246 |
| 84 | 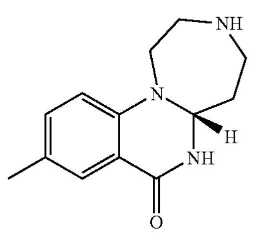 | 232 |
| 85 | 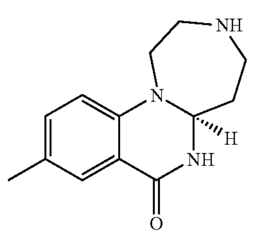 | 232 |
| 86 | 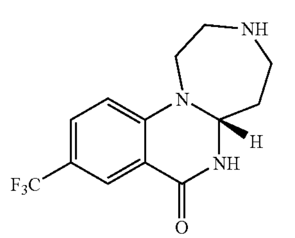 | 286 |
| 87 | 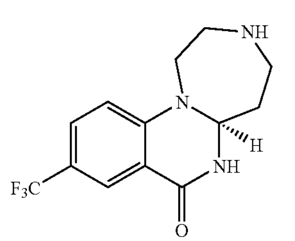 | 286 |
-continued
| Example No. | Structure | MS [M + H]+ |
|---|---|---|
| 88 | 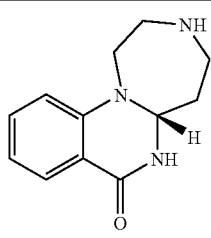 | 218 |
| 89 | 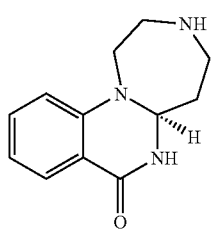 | 218 |
| 90 | 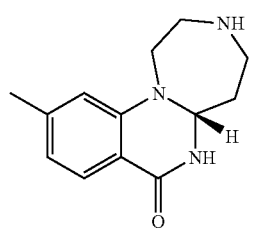 | 232 |
| 91 | 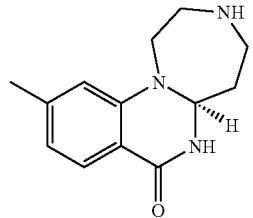 | 232 |
| 92 | 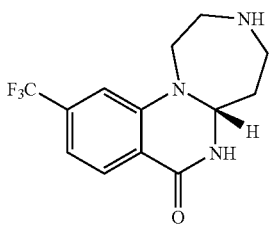 | 286 |
| 93 | 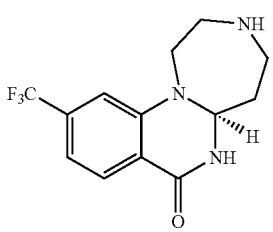 | 286 |

-continued
| Example No. | Structure | MS [M + H]+ |
|---|---|---|
| 94 | 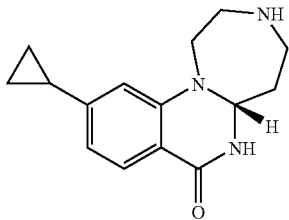 | 258 |
| 95 | 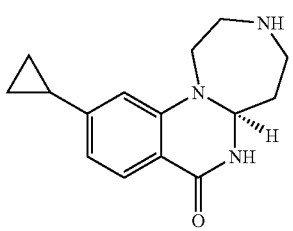 | 258 |
| 96 | 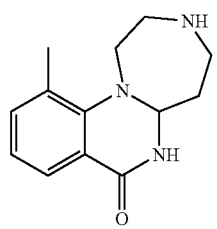 | 232 |
| 97 | 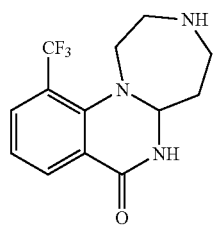 | 286 |
| 98 | 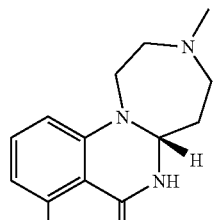 | 246 |
| 99 | 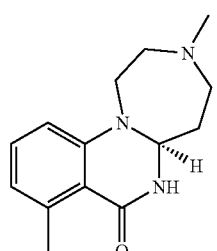 | 246 |
-continued
| Example No. | Structure | MS [M + H]+ |
|---|---|---|
| 100 | 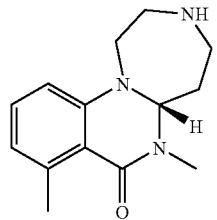 | 246 |
| 101 | 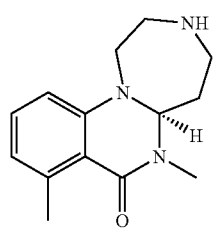 | 246 |
| 102 | 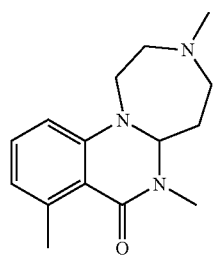 | 260 |
| 103 | 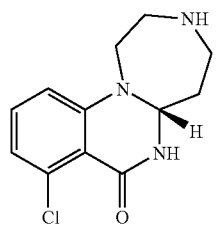 | 252 |
| 104 | 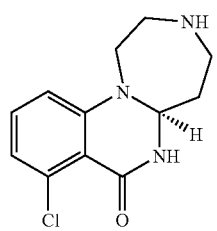 | 252 |
| 105 | 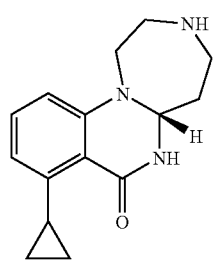 | 258 |

-continued
| Example No. | Structure | MS [M + H]+ |
|---|---|---|
| 106 | 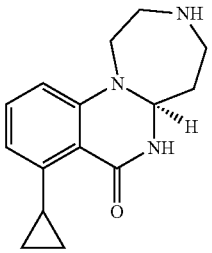 | 258 |
| 107 | 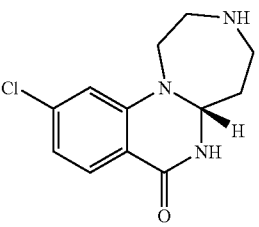 | 252 |
| 108 | 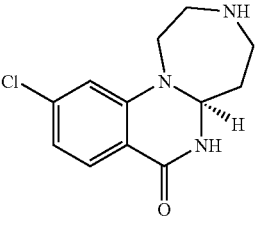 | 252 |
| 109 | 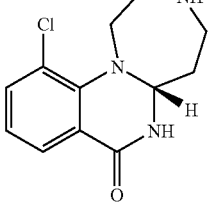 | 252 |
| 110 | 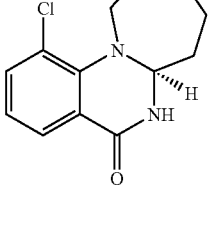 | 252 |
| 111 | 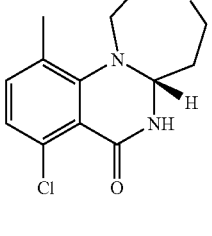 | 266 |
-continued
| Example No. | Structure | MS [M + H]+ |
|---|---|---|
| 112 | 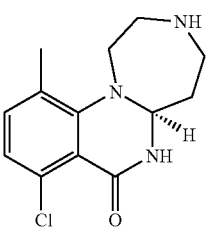 | 266 |
| 113 | 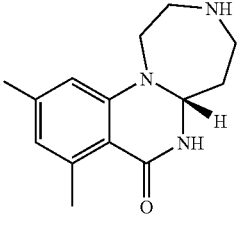 | 266 |
| 114 | 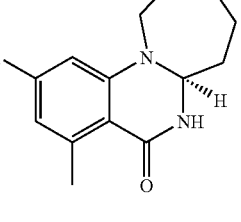 | 266 |
| 115 | 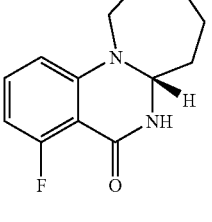 | 236 |
| 116 | 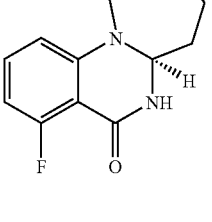 | 236 |
| 117 | 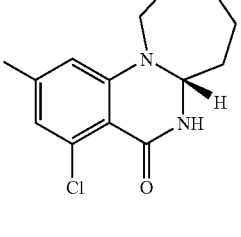 | 286 |

-continued
| Example No. | Structure | MS [M + H]+ |
|---|---|---|
| 118 | 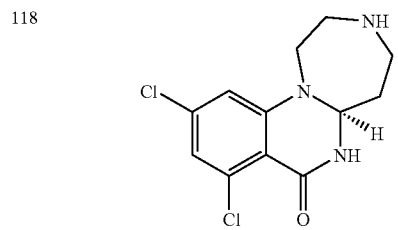 | 286 |
| 119 | 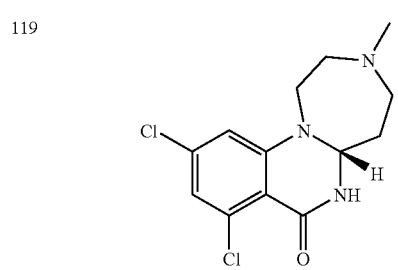 | 300 |
| 120 | 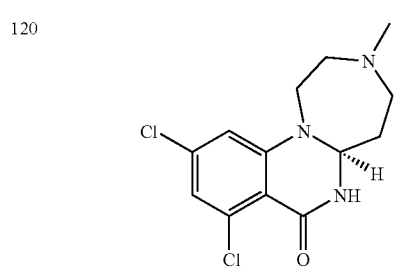 | 300 |
| 121 | 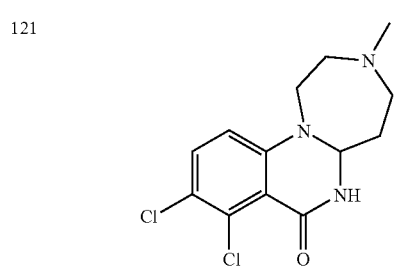 | 300 |
| 122 | 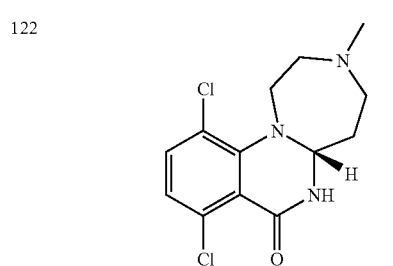 | 300 |
| 123 | 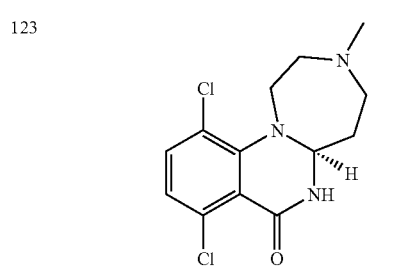 | 300 |
-continued
| Example No. | Structure | MS [M + H]+ |
|---|---|---|
| 124 | 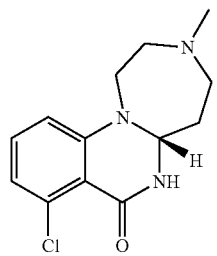 | 266 |
| 125 | 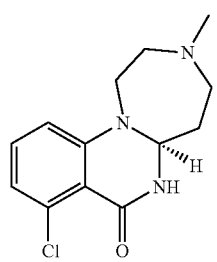 | 266 |
| 126 | 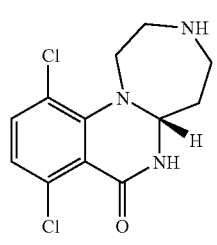 | 286 |
| 127 | 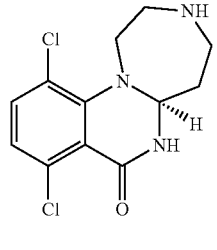 | 286 |
| 128 | 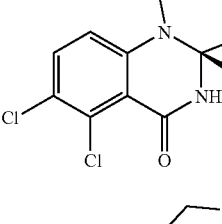 | 300 |
| 129 | 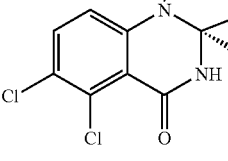 | 300 |

-continued

| Example No. | Structure | MS [M + H]+ |
|---|---|---|
| 130 | 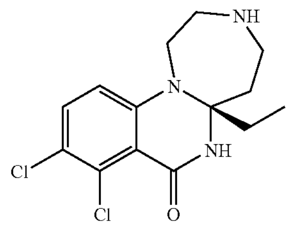 | 314 |
| 131 | 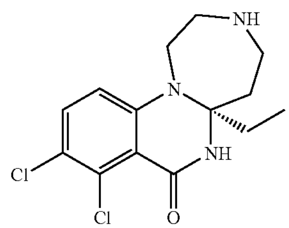 | 314 |
| 132 | 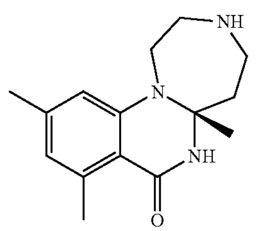 | 260 |
| 133 | 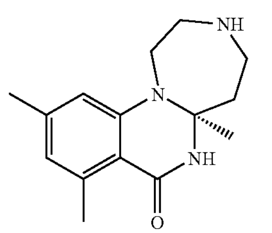 | 260 |
| 134 | 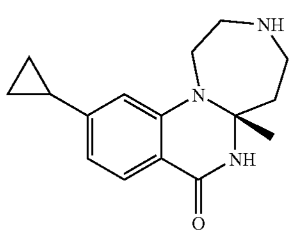 | 272 |
| 135 | 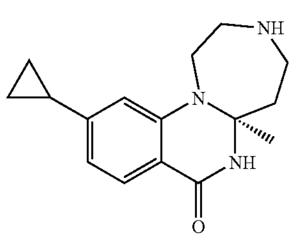 | 272 |

-continued

| Example No. | Structure | MS [M + H]+ |
|---|---|---|
| 136 | 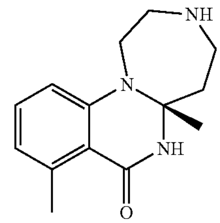 | 245 |
| 137 | 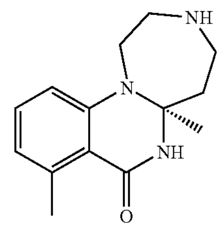 | 245 |
| 138 | 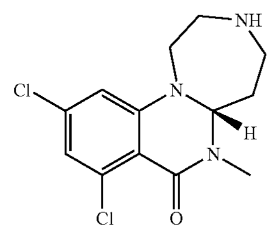 | 300 |
| 139 | 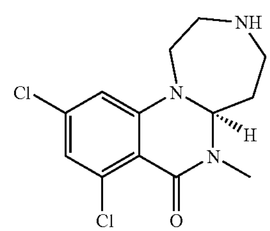 | 300 |
| 140 | 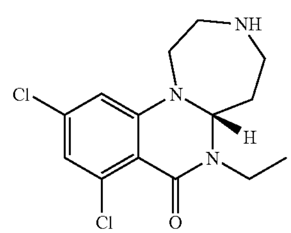 | 314 |
| 141 | 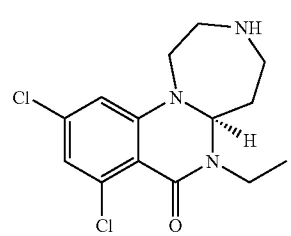 | 314 |

| Example No. | Structure | MS [M + H]+ |
|---|---|---|
| 142 | 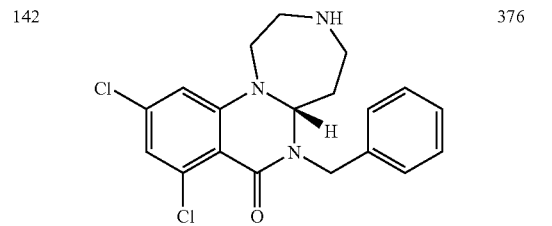 | 376 |
| 143 | 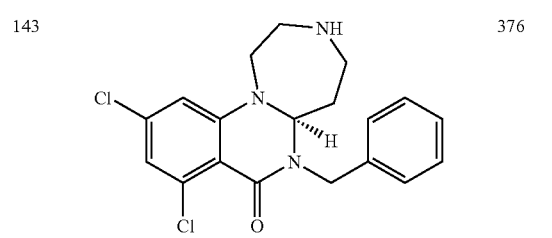 | 376 |
| 144 | 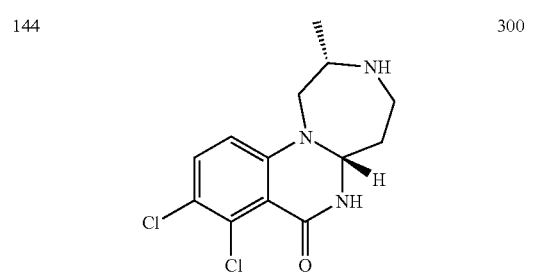 | 300 |
| 145 | 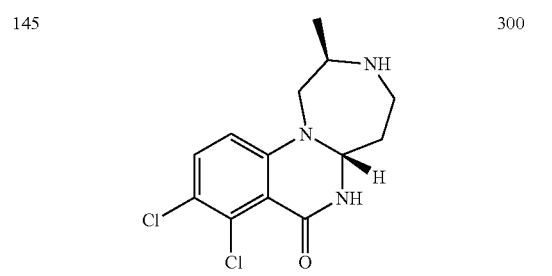 | 300 |
| 146 | 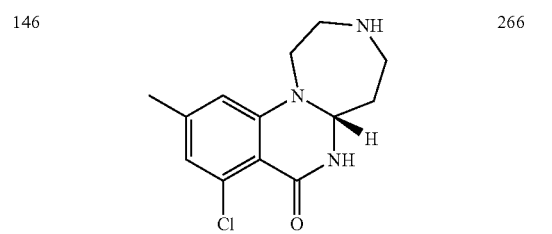 | 266 |
| 147 | 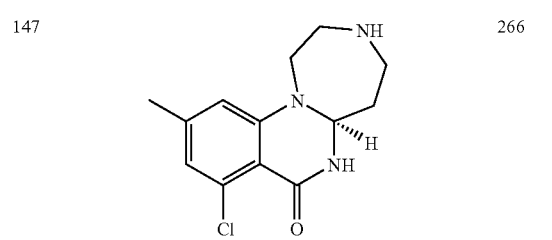 | 266 |
| Example No. | Structure | MS [M + H]+ |
|---|---|---|
| 148 | 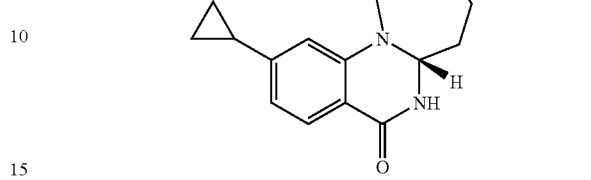 | 272 |
| 149 | 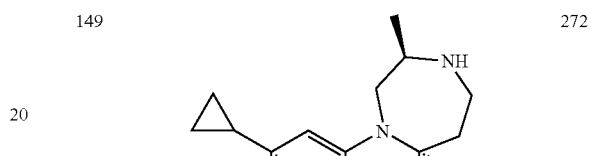 | 272 |
| 150 |  | 272 |
| 151 | 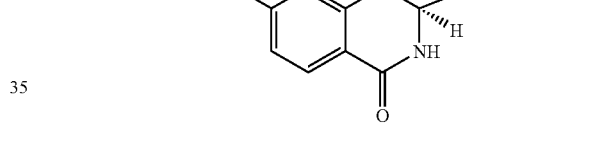 | 272 |
| 152 | 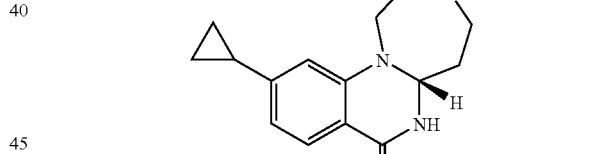 | 250 |
| 153 | 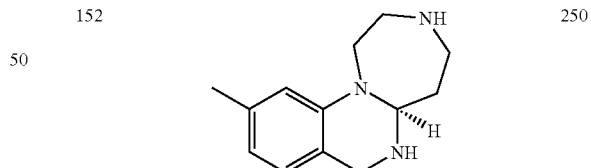 | 250 |

-continued
| Example No. | Structure | MS [M + H]⁺ |
|---|---|---|
| 154 | 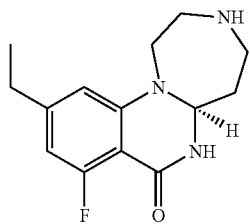 | 264 |
| 155 | 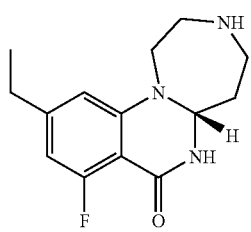 | 264 |
| 156 | 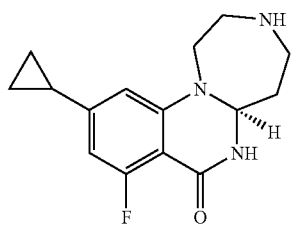 | 276 |
| 157 | 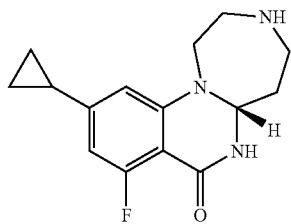 | 276 |
| 158 | 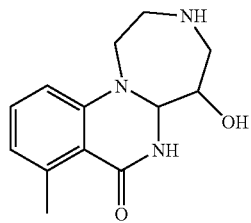 | 248 |
| 159 | 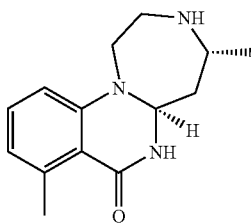 | 246 |
-continued
| Example No. | Structure | MS [M + H]⁺ |
|---|---|---|
| 160 | 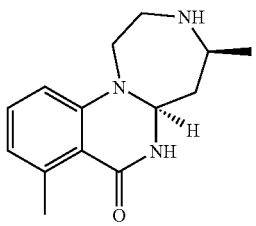 | 246 |
| 161 | 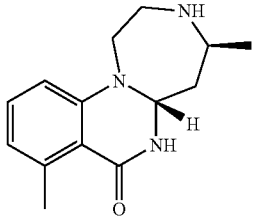 | 246 |
| 162 | 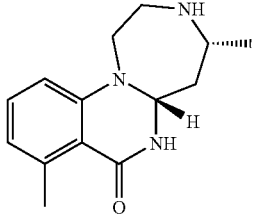 | 246 |
| 163 | 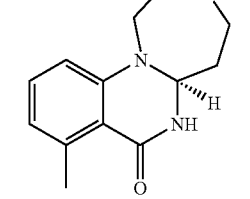 | 246 |
| 164 | 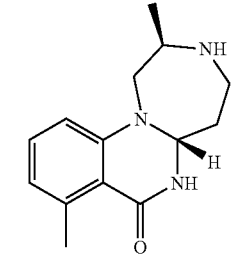 | 246 |
| 165 | 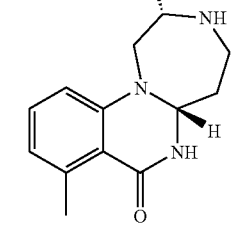 | 246 |

-continued

| Example No. | Structure | MS [M + H]+ |
|---|---|---|
| 166 | 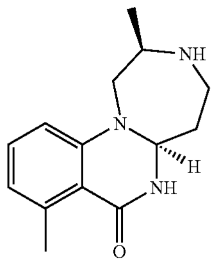 | 246 |
| 167 | 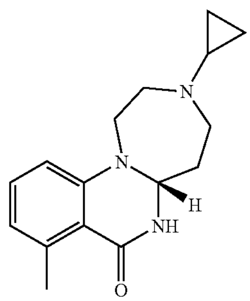 | 272 |
| 168 | 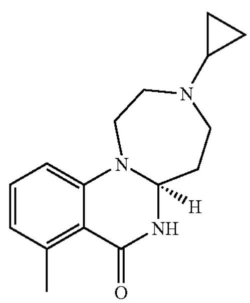 | 272 |

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

A number of references have been cited and the entire disclosures of which are incorporated herein by reference.

What is claimed is:

1. A compound according to Formula I:

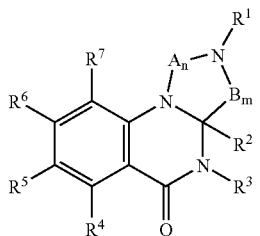

including all stereoisomers and salts thereof, wherein
A is $CR^{1a}R^{1b}$;
B is $CR^{1c}R^{1d}$;
m is 1 or 2;
n is 2 or 3;
$R^1$, $R^{1a}$, $R^{1b}$, $R^{1c}$, $R^{1d}$ and $R^2$ are independently selected from the group consisting of H, alkyl, alkenyl, alkynyl, cycloalkyl, heterocyclyl, aryl and heteroaryl;
$R^3$ is selected from the group consisting of H, alkyl, alkenyl, alkynyl, cycloalkyl, heterocyclyl, aryl and heteroaryl;
$R^4$, $R^5$, $R^6$ and $R^7$ are independently selected from the group consisting of H, hydroxy, alkyl, alkenyl, alkynyl, oxyalkyl, oxyalkenyl, oxyalkynyl, oxycycloalkyl, oxyperfluoroalkyl, thioalkyl, thioalkenyl, thioalkynyl, thioaryl, thioheteroaryl, thiocycloalkyl, aryl, heteroaryl, heterocyclyl, nitrile, halogen, carboaminoalkyl, carboaminoalkenyl, carboaminoalkynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, perfluoroalkyl, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, sulfonylalkyl, sulfonylaryl, sulfonylamino, aminosulfonylalkyl, alkylcycloalkyl and cycloalkyl,
wherein independently $R^1$, $R^{1a}$, $R^{1b}$, $R^{1c}$, $R^{1d}$, $R^2$, $R^3$, $R^4$, $R^5$, $R^6$ and $R^7$ may optionally be substituted with one or more hydroxy, alkyl, alkenyl, alkynyl, oxyalkyl, oxyalkenyl, oxyalkynyl, oxycycloalkyl, oxyperfluoroalkyl, thioalkyl, thioalkenyl, thioalkynyl, thioaryl, thioheteroaryl, thiocycloalkyl, aryl, heteroaryl, heterocyclyl, amino, nitrile, halogen, carboaminoalkyl, carboaminoalkenyl, carboaminoakynyl, carboaminoaryl, carboaminocycloalkyl, carboheterocyclyl, carboheteroaryl, carboaminoheterocyclyl, carboaminoheteroaryl, aminocarboalkyl, aminocarboalkenyl, aminocarboalkynyl, aminocarboaryl, aminocarbocycloalkyl, aminocarboheterocyclyl, aminocarboheteroaryl, oxycarboaminoalkyl, oxycarboaminoalkenyl, oxycarboaminoalkynyl, oxycarboaminoaryl, oxycarboaminocycloalkyl, oxycarboaminoheterocyclyl, oxycarboaminoheteroaryl, aminocarboxyalkyl, aminocarboxyalkenyl, aminocarboxyalkynyl, aminocarboxyaryl, aminocarboxycycloalkyl, aminocarboxyheterocyclyl, aminocarboxyheteroaryl, aminocarboaminoalkyl, aminocarboaminoalkenyl, aminocarboaminoalkynyl, aminocarboaminoaryl, aminocarboaminocycloalkyl, aminocarboheterocyclyl, aminocarboheteroaryl, aminocarboaminoheterocyclyl, aminocarboaminoheteroaryl, perfluoroalkyl, perfluoroalkenyl, perfluoroalkynyl, oxyaryl, oxyheteroaryl, aminoalkyl, aminoalkenyl, aminoalkynyl, aminoaryl, aminoheteroaryl, aminocycloalkyl, alkylamino, alkenylamino, alkynylamino, arylamino, heteroarylamino, cycloalkylamino, carboxyalkyl, carboxyalkenyl, carboxyalkynyl, carboxyaryl, carboxyheteroaryl, carboxycycloalkyl, oxycarboalkyl, oxycarboalkenyl, oxycarboalkynyl, oxycarboaryl, oxycarboheteroaryl, oxycarbocycloalkyl, sulfonylalkyl, sulfonylaryl, sulfonylamino, aminosulfonylalkyl, alkylcycloalkyl and cycloalkyl, wherein $R^4$ and $R^5$, $R^5$ and $R^6$ or $R^6$ and $R^7$ may be taken together to form a 5- to 8-membered cycloalkyl, aryl, heterocyclyl or heteroaryl.

2. The compound according to claim 1, wherein
$R^1$ and $R^2$ are selected from the group consisiting of H, alkyl and cycloalkyl.

3. The compound according to claim 2, wherein
$R^4$, $R^5$, $R^6$ and $R^7$ are selected from the group consisting of H, alkyl, cycloalkyl, perfluoroalkyl, halo, aryl and alkoxy.

4. The compound according to claim 3, wherein
the halo is selected from the group consisting of chloro, bromo and fluoro.

5. The compound according to claim 1, wherein the compound is selected from the group consisting of

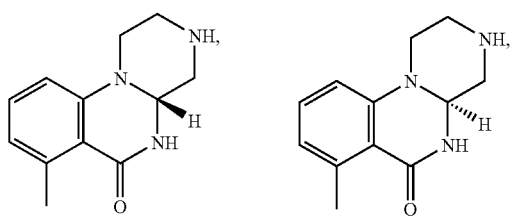

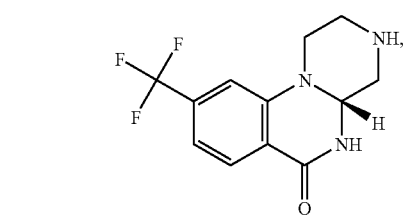

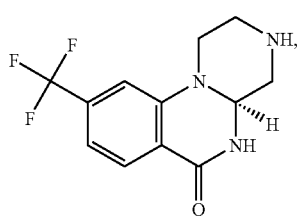

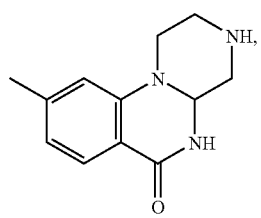

-continued

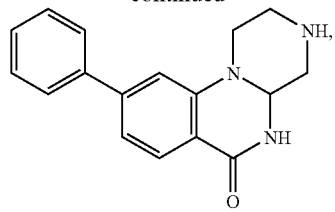

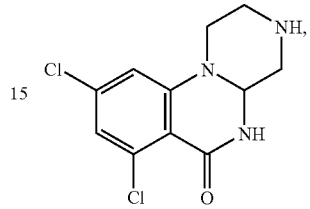
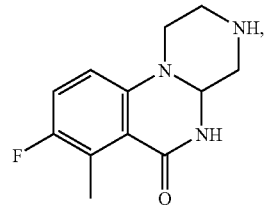

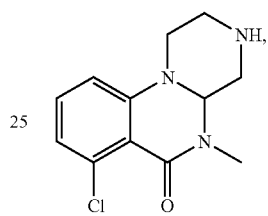
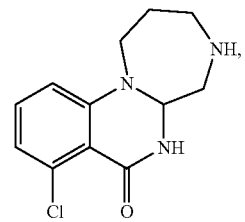

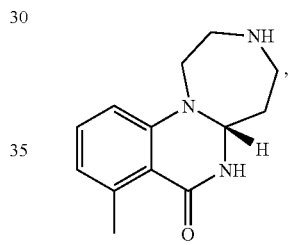

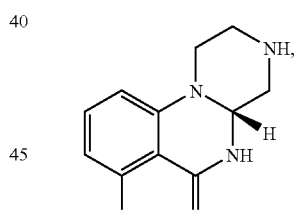

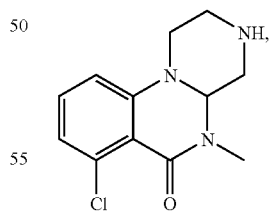

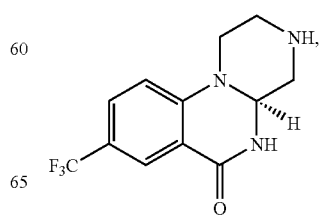

-continued
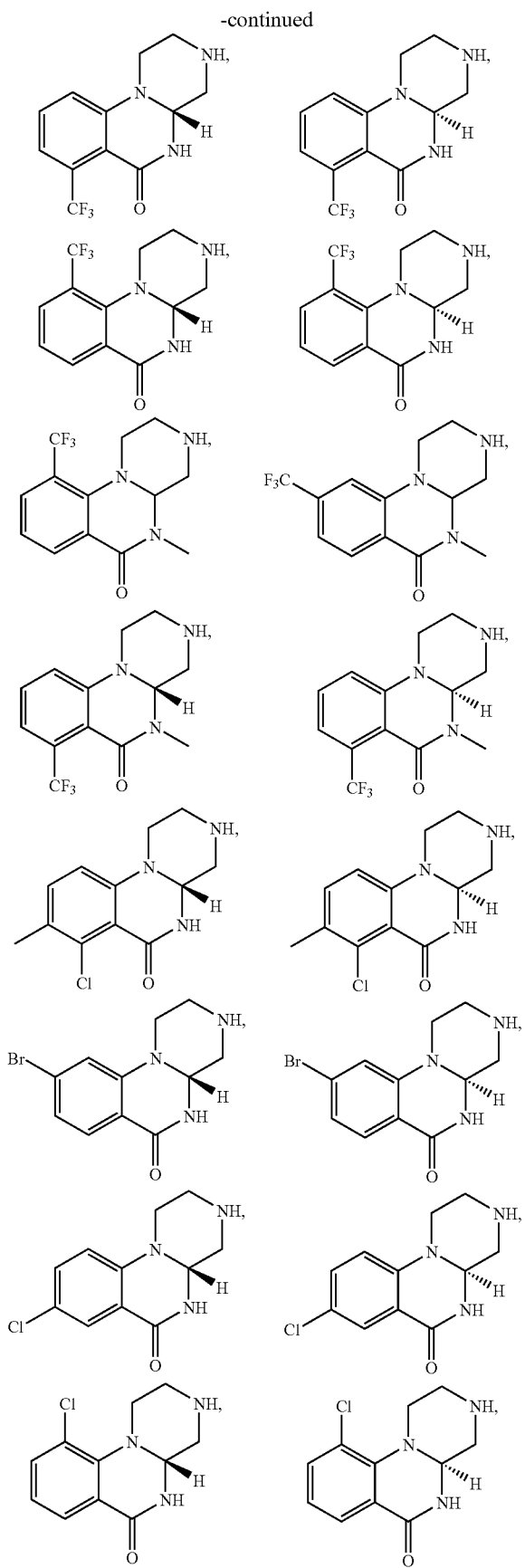
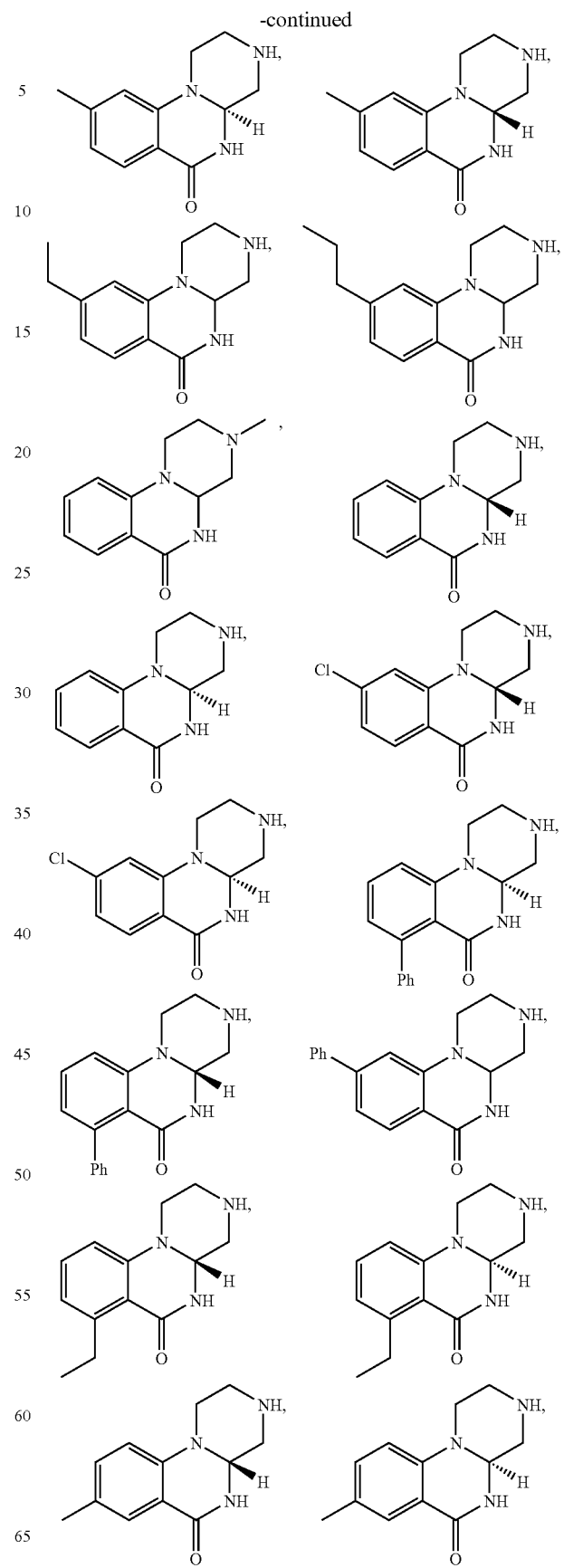

-continued
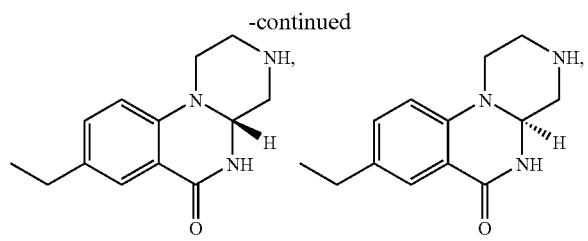
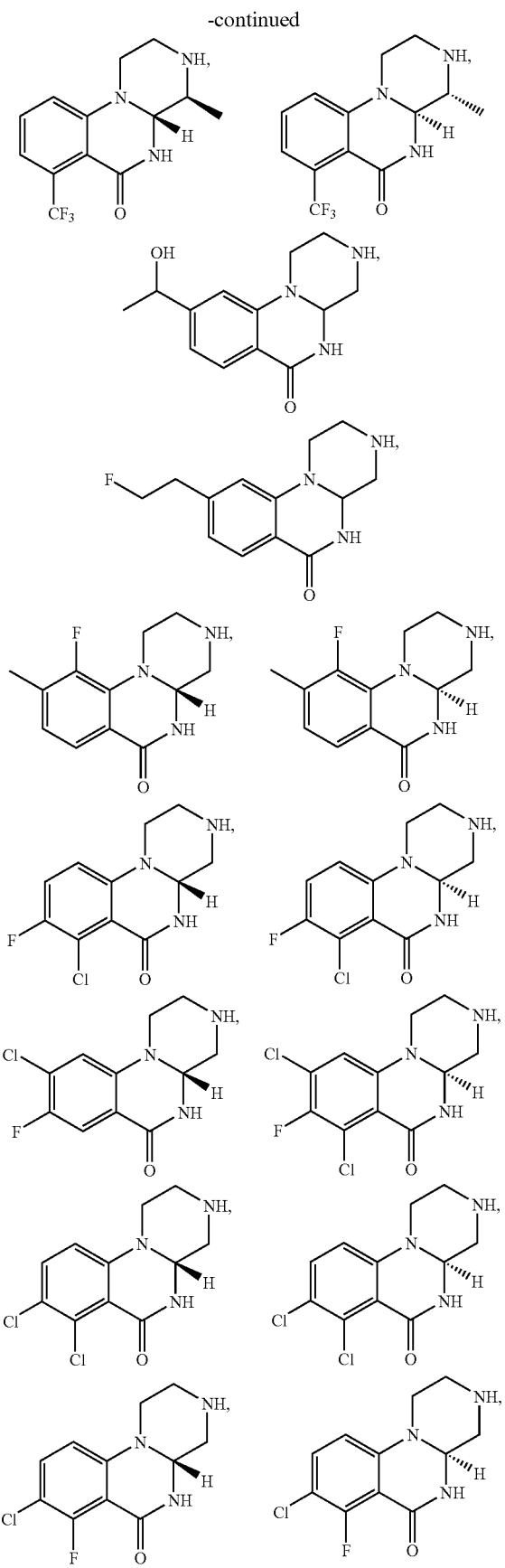

-continued
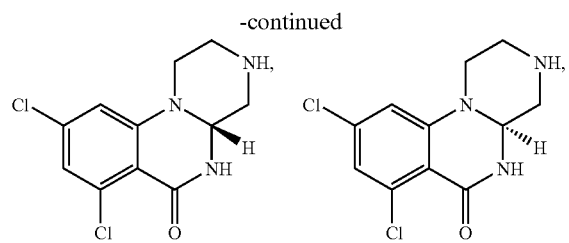
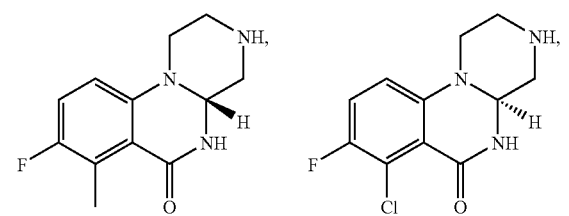
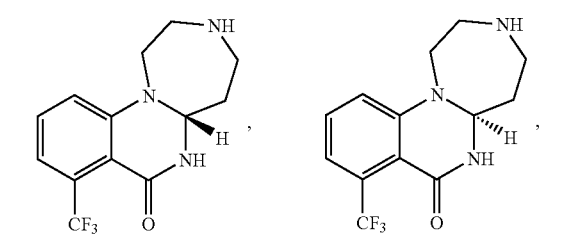
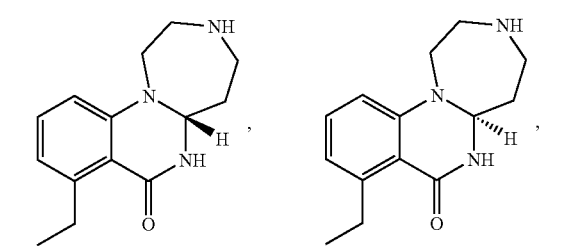
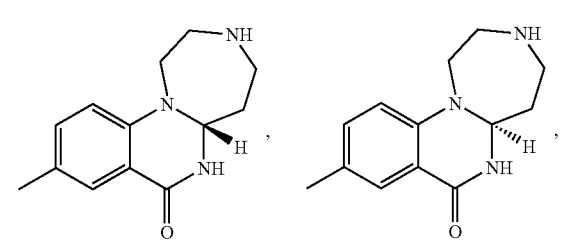
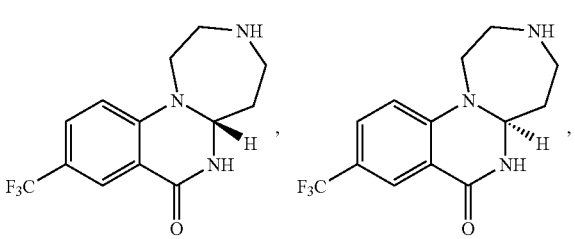
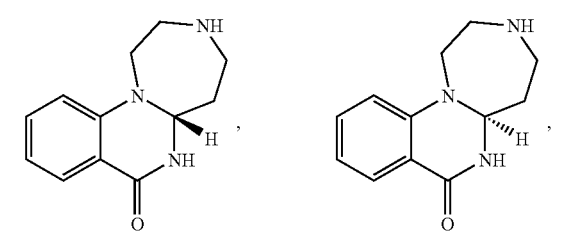
-continued
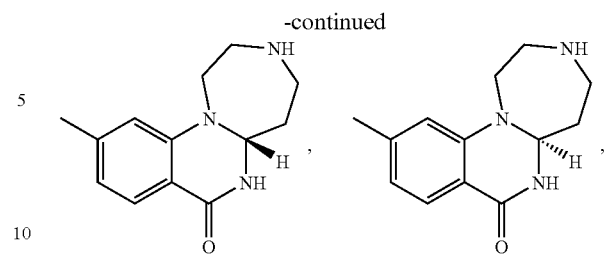
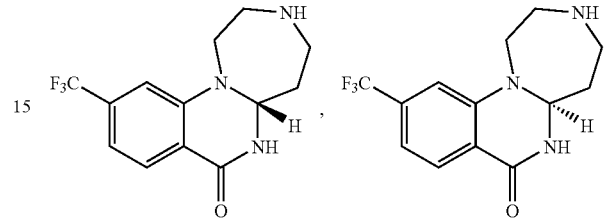
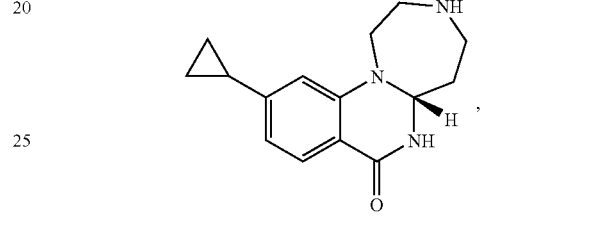
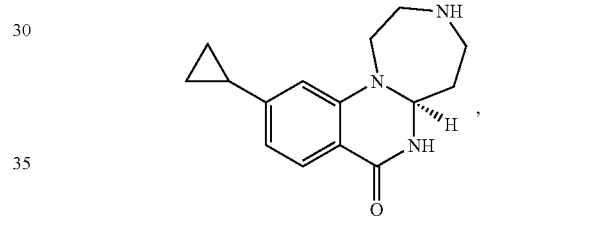
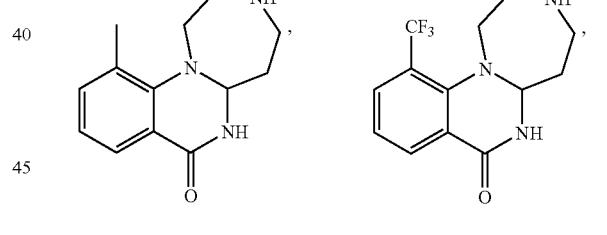
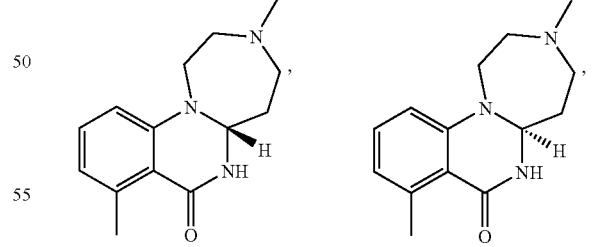
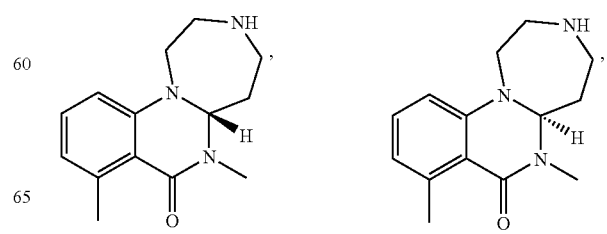

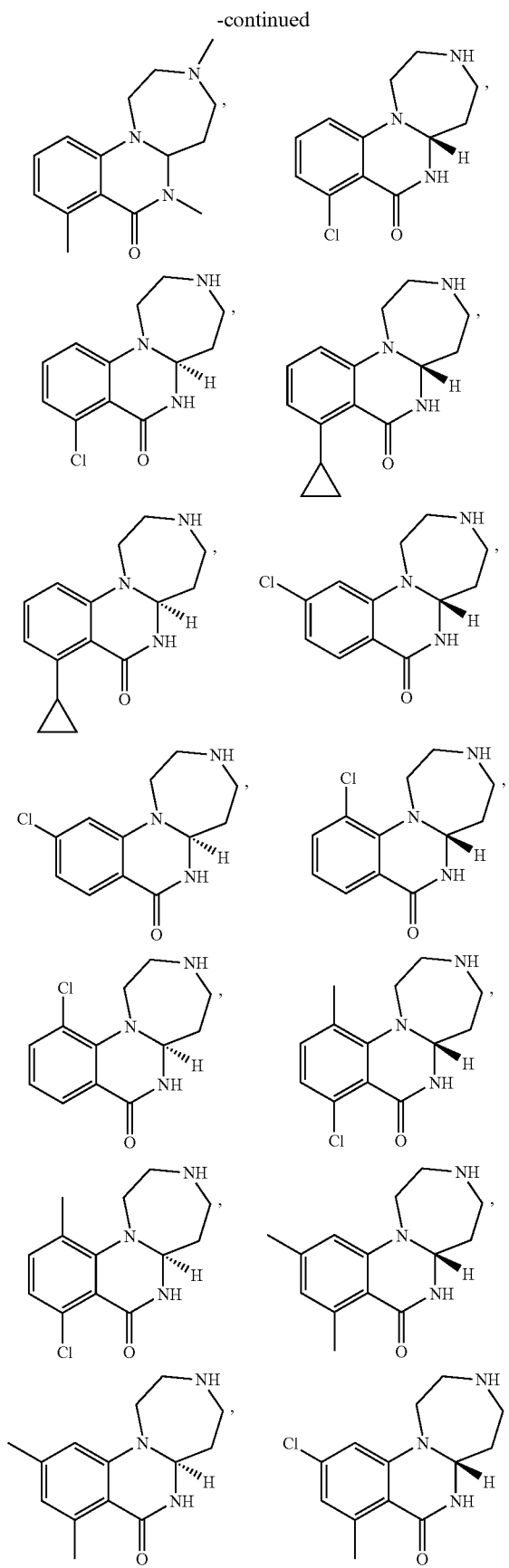
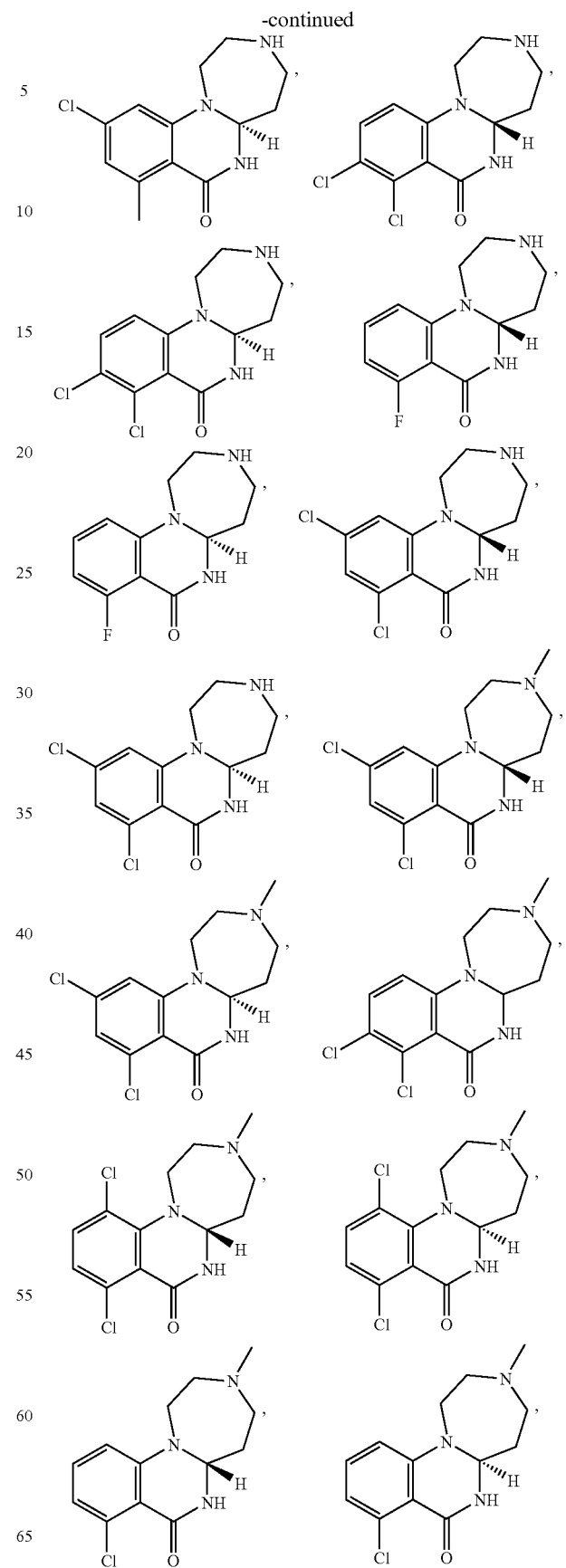

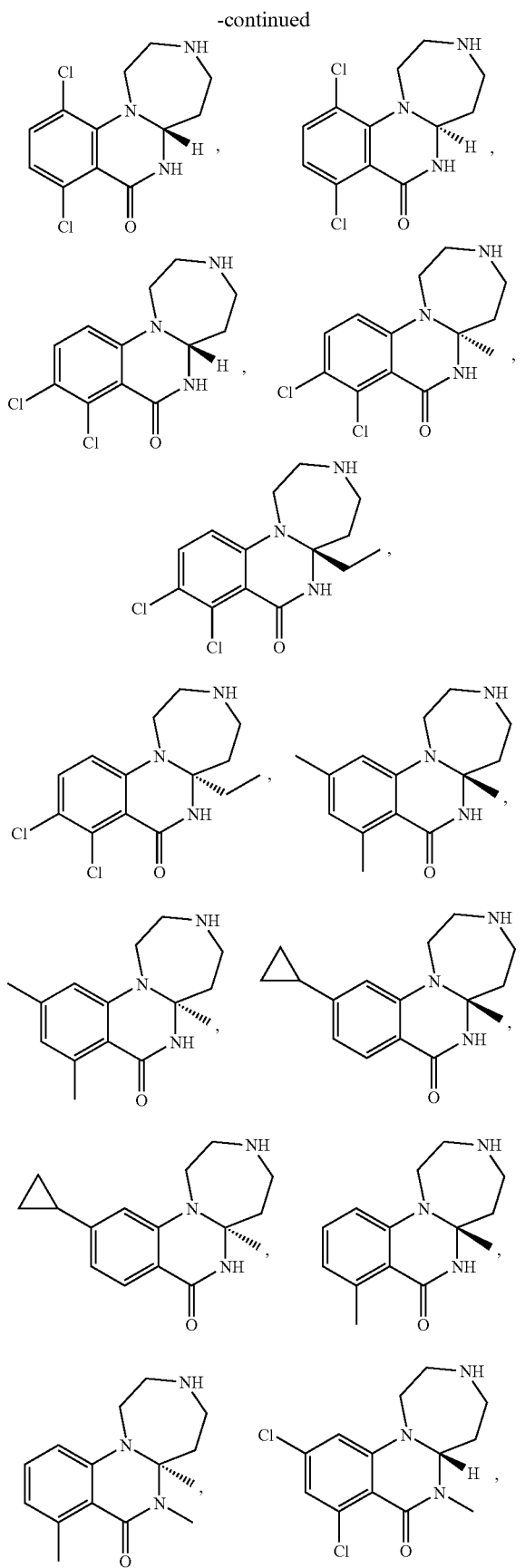
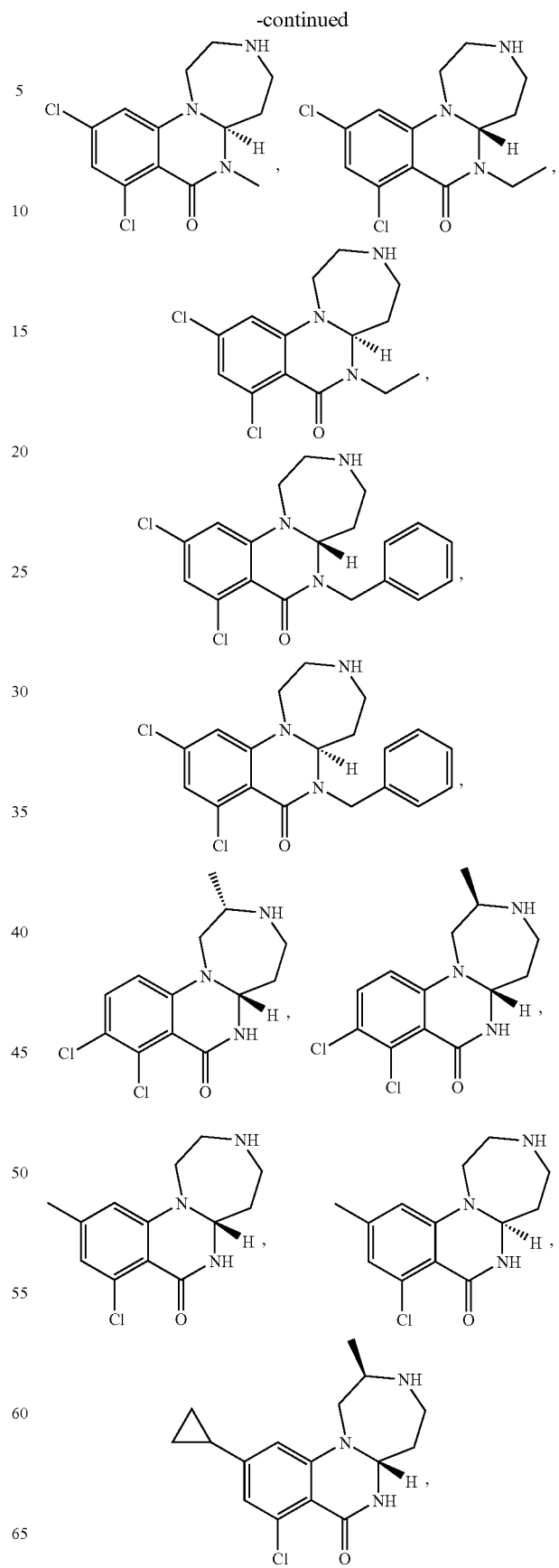

-continued

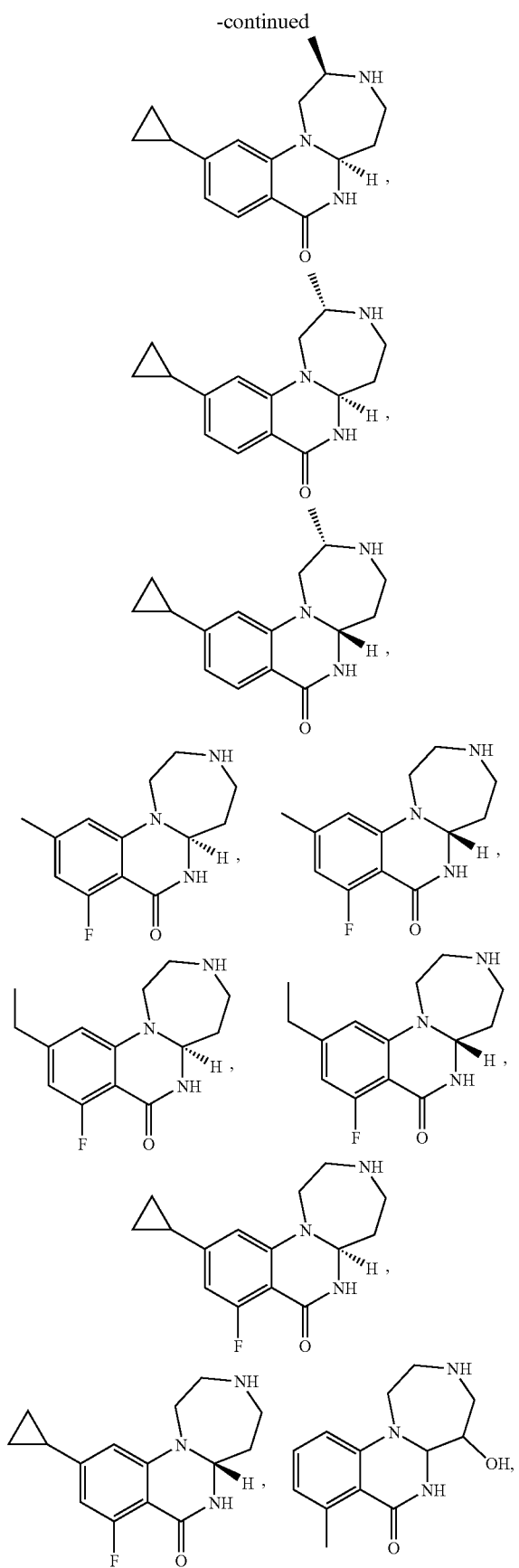

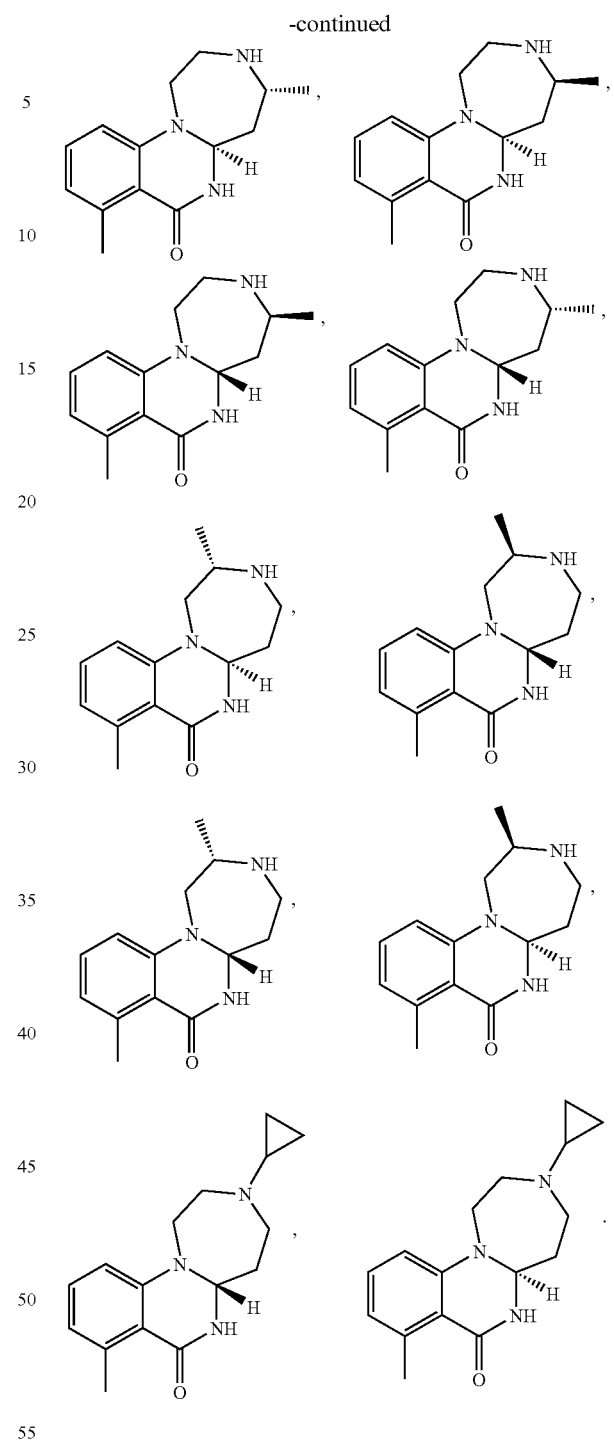

6. A pharmaceutical composition, comprising:
   a compound according to claim 1; and
   a pharmaceutically adjuvant or carrier.

7. The pharmaceutical composition according to claim 6, further comprising:
   at least one additional therapeutic agent.

8. A method of treating obesity by administering to a mammal in need of treatment a therapeutically effective amount of a compound according to claim 1.

* * * * *

UNITED STATES PATENT AND TRADEMARK OFFICE
CERTIFICATE OF CORRECTION

PATENT NO. : 7,238,702 B2 Page 1 of 1
APPLICATION NO. : 11/350997
DATED : July 3, 2007
INVENTOR(S) : Ahmad et al.

It is certified that error appears in the above-identified patent and that said Letters Patent is hereby corrected as shown below:

In Column 71, Lines 11-20

" 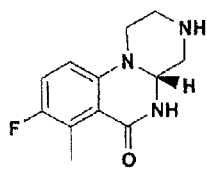 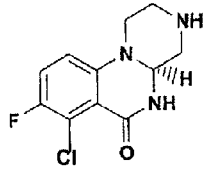 "

Should read:

-- 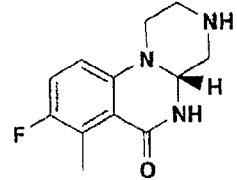 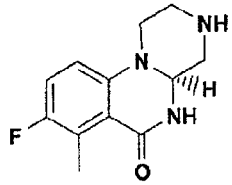 --

Signed and Sealed this

Seventeenth Day of June, 2008

JON W. DUDAS
*Director of the United States Patent and Trademark Office*